US005512490A

United States Patent [19]
Walt et al.

[11] Patent Number: 5,512,490
[45] Date of Patent: Apr. 30, 1996

[54] OPTICAL SENSOR, OPTICAL SENSING APPARATUS, AND METHODS FOR DETECTING AN ANALYTE OF INTEREST USING SPECTRAL RECOGNITION PATTERNS

[75] Inventors: David R. Walt, Lexington; John S. Kauer, Weston, both of Mass.

[73] Assignee: Trustees of Tufts College, Medford, Mass.

[21] Appl. No.: 289,001

[22] Filed: Aug. 11, 1994

[51] Int. Cl.[6] .................................................. G01N 21/77
[52] U.S. Cl. ........................ 436/171; 422/82.05; 422/91; 356/317; 250/459.1
[58] Field of Search ............................ 422/82.06, 82.07, 422/82.05, 82.08, 86, 91; 436/171, 172, 164; 250/458.1, 271, 461.1, 461.2, 459.1; 356/317, 318, 417

[56] References Cited

U.S. PATENT DOCUMENTS

| | | |
|---|---|---|
| 4,582,809 | 4/1986 | Block et al. . |
| 4,785,814 | 11/1988 | Kane . |
| 4,822,746 | 4/1989 | Walt . |
| 4,842,783 | 6/1989 | Blaylock . |
| 4,919,891 | 4/1990 | Yafuso et al. . |
| 4,925,268 | 3/1990 | Iyer et al. . |
| 4,999,306 | 3/1991 | Yafuso et al. . |
| 5,019,350 | 5/1991 | Rhum et al. . |
| 5,047,627 | 9/1991 | Yim et al. . |
| 5,114,864 | 5/1992 | Walt . |
| 5,143,853 | 9/1992 | Walt . |
| 5,152,287 | 10/1992 | Kane . |
| 5,244,636 | 9/1993 | Walt et al. . |
| 5,244,813 | 9/1993 | Walt et al. . |
| 5,250,264 | 10/1993 | Walt et al. . |
| 5,252,494 | 10/1993 | Walt . |
| 5,298,741 | 3/1994 | Walt et al. . |
| 5,320,814 | 6/1994 | Walt et al. . |

OTHER PUBLICATIONS

Olness, D. et al, Report (1984) UCID–20047 Chem. Abstracts AN 1986:490265 (Abstract Only).
Smardzewski, Talanta (1988), 35(2) 95–101 Abstract Only.
Yokoyama, K. & F. Ebisawa, Anal. Chem. 65:673–677 (1993).
Patrash, S. J. & E. T. Zellers, Anal. Chem. 65:2055–2066 (1993).
Grate et al., Anal. Chem. 65:1868–1881 (1993).

Primary Examiner—Jeffrey R. Snay
Attorney, Agent, or Firm—David Prashker

[57] ABSTRACT

The present invention is an optical detection and identification system and provides an optic sensor, an optic sensing apparatus and methodology for detecting and evaluating one or more analytes or ligands of interest, either alone or in admixture. The optic sensor of the system is comprised of a supporting member and an array formed of heterogeneous, semi-selective thin films which function as sensing receptor units and are able to detect a variety of different analytes and ligands using spectral recognition patterns.

6 Claims, 20 Drawing Sheets

FIG. I

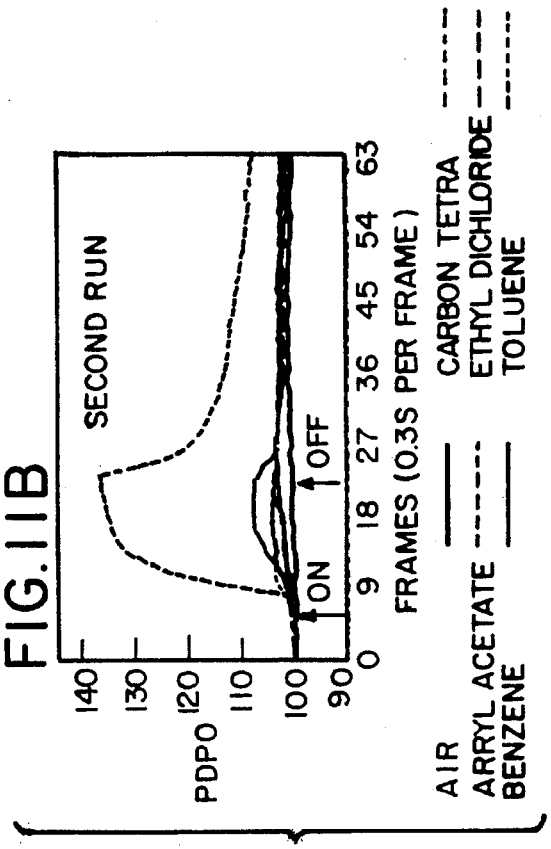
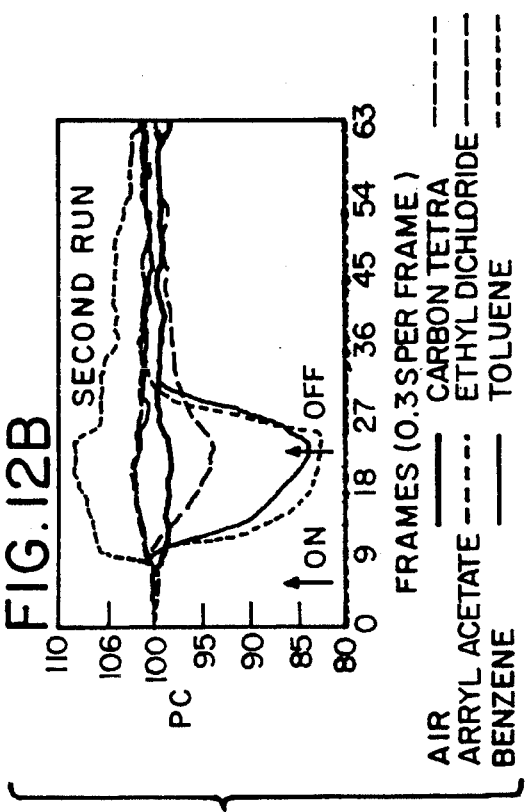
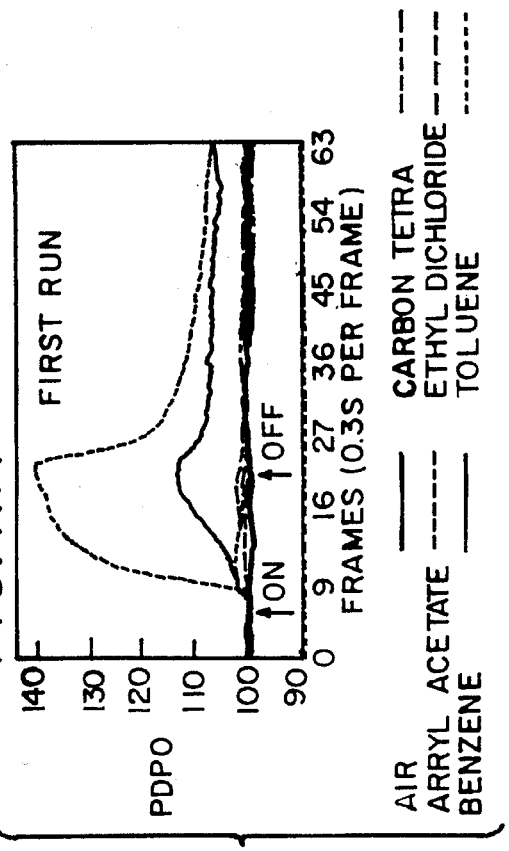
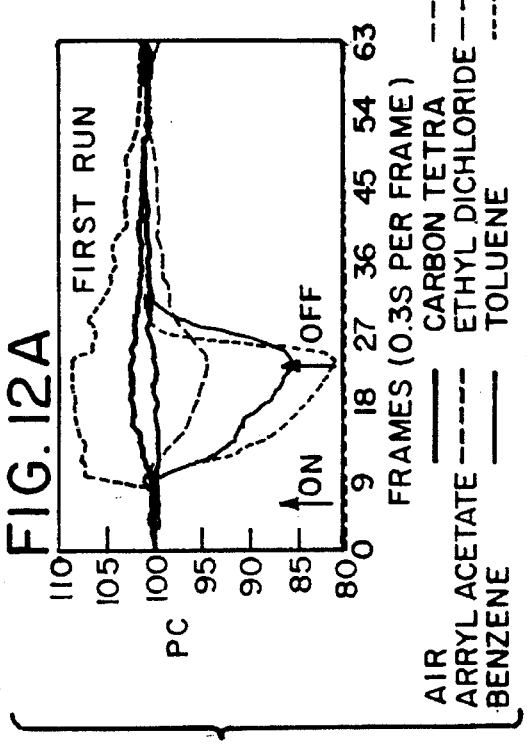

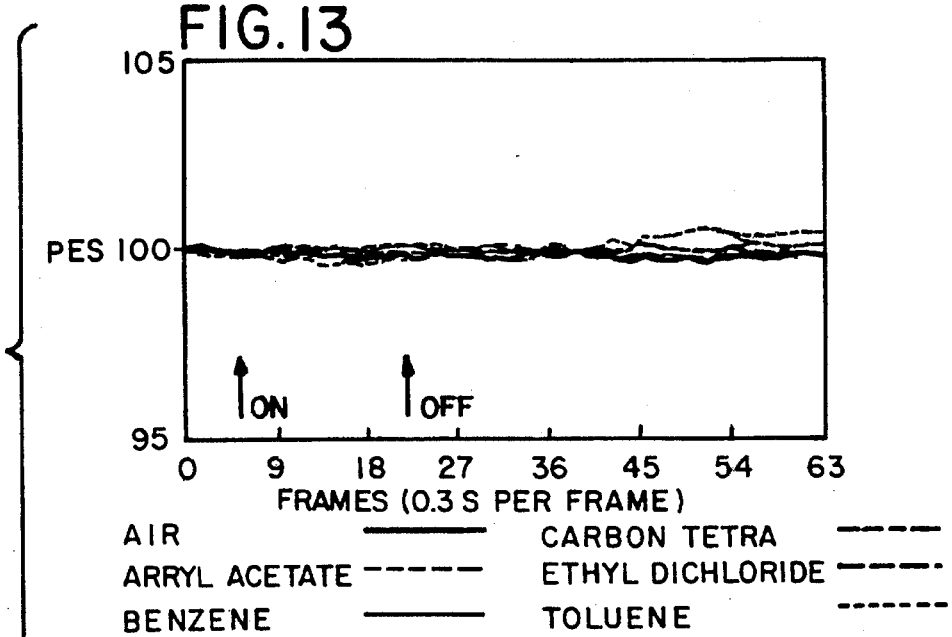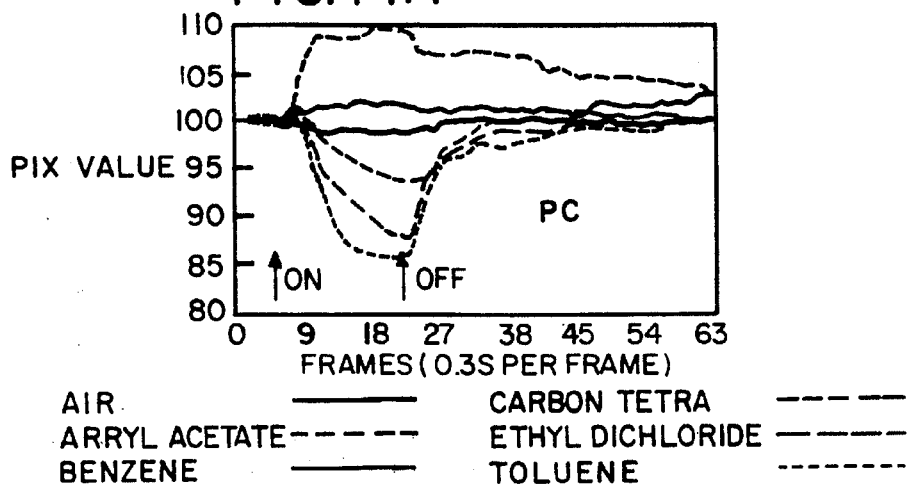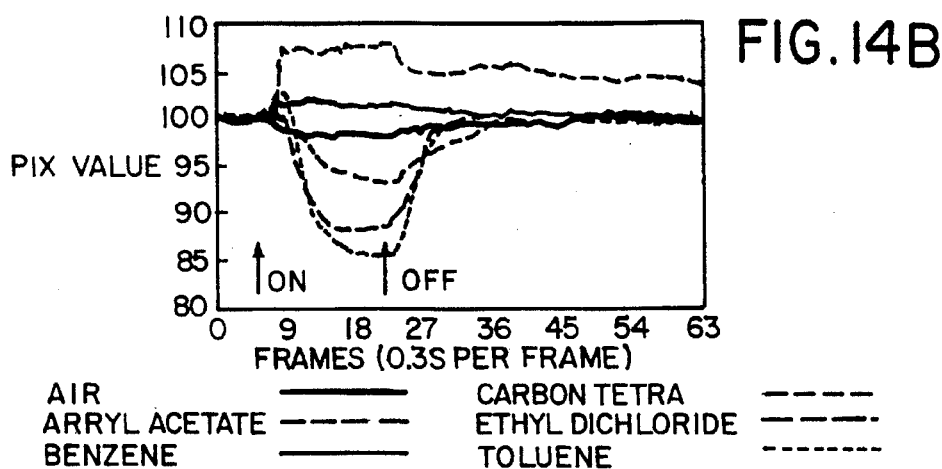

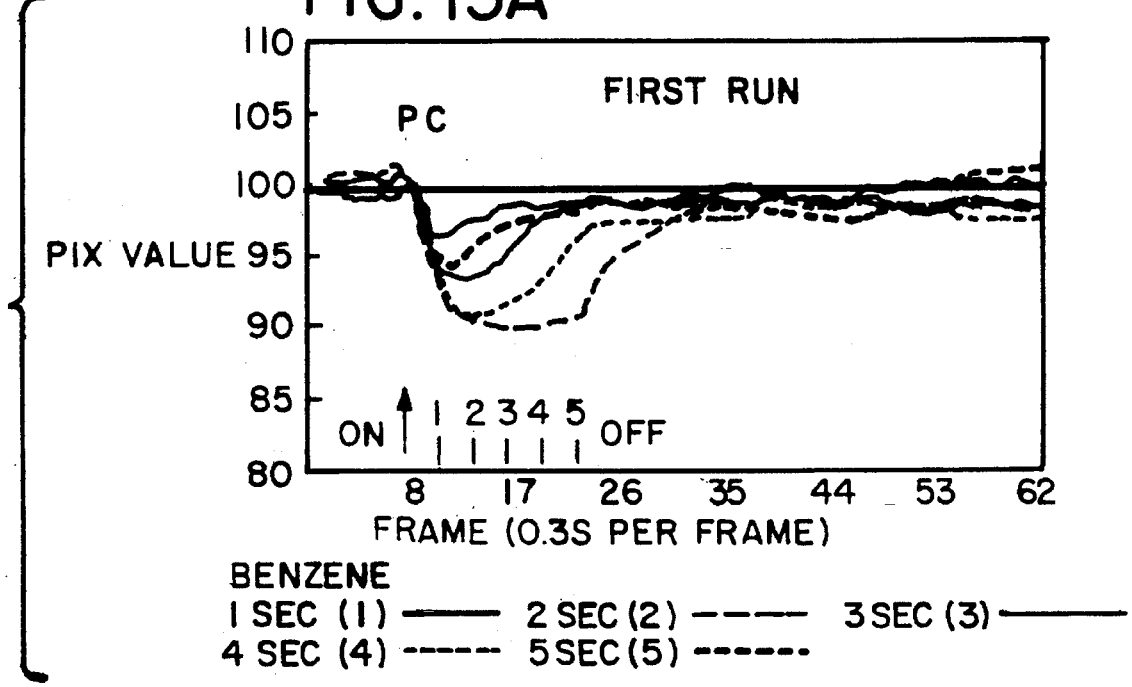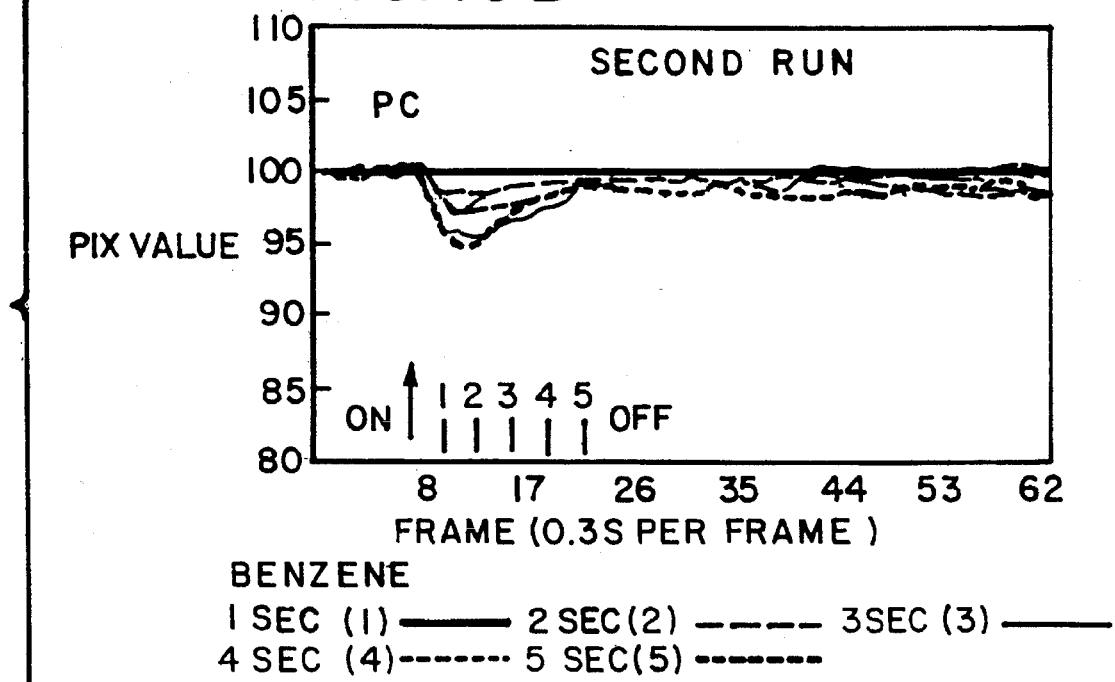

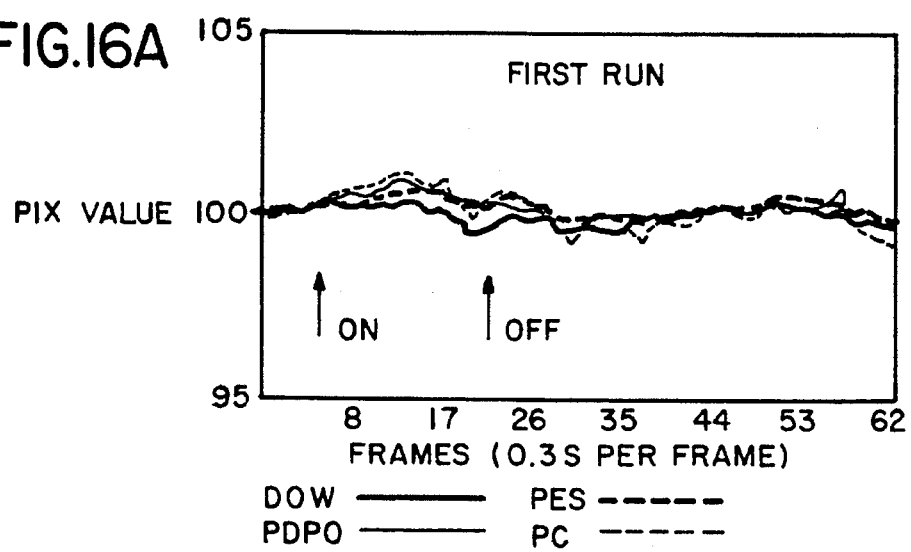
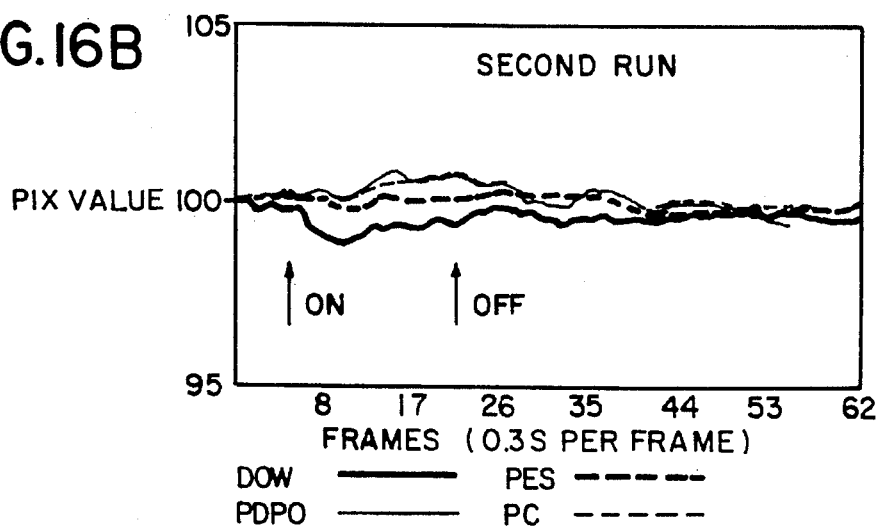
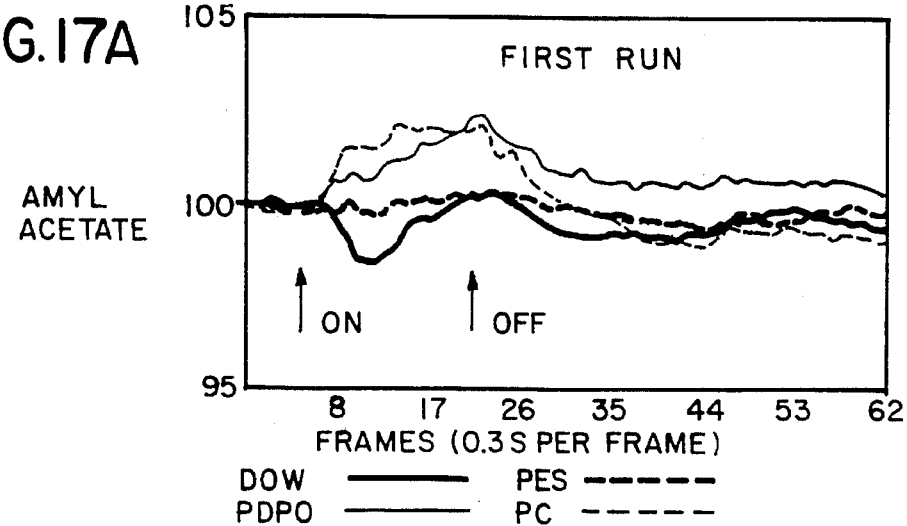

OPTICAL SENSOR, OPTICAL SENSING APPARATUS, AND METHODS FOR DETECTING AN ANALYTE OF INTEREST USING SPECTRAL RECOGNITION PATTERNS

FIELD OF THE INVENTION

The present invention is concerned with optical chemical sensors and sensing apparatus for the detection of gaseous and liquid analytes in a manner analogous to the mammalian olfactory system; and is particularly directed to the use of pattern recognition techniques for detection and evaluation of optical data generated by an array of thin film, semi-selective sensing receptor units.

BACKGROUND OF THE INVENTION

In the last ten to fifteen years, intensive efforts and developments have occurred in chemical sensor research and in chemical sensing detection methods and instruments for occupational safety, environmental monitoring, and for processing or quality control. Optical sensors and sensing apparatus have been of particular interest; and the use of optical fibers and optical fiber strands in combination with light energy absorbing dyes for medical, biochemical, and chemical analytical determinations has undergone rapid development.

Conventional optical sensors and optical sensing apparatus, whether or not optical fibers are used, typically employ one or more light energy absorbing dyes which are specific for an analyte of interest and will selectively bind with that analyte. Thus, when light of an appropriate wavelength is introduced to and has been absorbed by the dye, the light energy which is either not absorbed or is returned as an emission is observed and measured by a detection system. The interactions between the light energy conveyed and the properties of the specifically—binding, light absorbing dye—in the presence of one or more ligands or analytes of interest and in the absence of any ligands or analytes whatsoever-provide an optical basis for both qualitative and quantitative determinations. This traditional approach, for both optical and non-optical sensors alike, has therefore been to create highly selective sensors by finding and using specific binding materials. This overall approach consequently results in creating one sensor for each analyte or ligand of interest to be detected. The one analyte/one sensor approach thus has been previously and remains today the overriding guiding principle and axiom for optical chemical sensors and optical chemical sensing apparatus.

It is useful to recognize and appreciate the stringent demands and essential requirements of the traditional one analyte/one sensor approach. These include: (1) each sensor must employ and use one highly selective/specific binding agent for binding and reaction with a single analyte or ligand of interest in a sample; (2) the sensor relies and depends upon the energy signal generated by the selective binding agent as the means for detecting and determining the presence of the single analyte or ligand in the sample; (3) the approach requires that for detection of multiple analytes or ligands, a series of different selective binding agents with individual and different binding specificities are used together as multiples concurrently or in sequence; and (4) the specific binding and signal generation of the sensor can be accomplished using a variety of different binding agents including colorimetric or fluorescent dyes, selective polymer films, or biological receptors such as enzymes and antibodies. In each instance, one sensor must be created for the detection of each analyte or ligand of interest.

In comparison, it will be noted that nature has created a biological sensing system which is markedly different both in structure and function from the man-made traditional chemical sensor approach. For example, the mammalian olfactory system is an in-vivo sensor for vaporous odors which is not matched by any artificially synthesized sensor to date in detection limit and discriminatory power. Vapor odor reception is an interaction between olfactory receptor cells and the vapor molecules. In short, the odor is "sensed" by sensory neurons in the olfactory epithelium, followed by the formation of a neuronal activity pattern which consists from multiple different responses of receptor cells to the one odor. The activity pattern of affected sensory neurons is projected to the olfactory bulb; and the response patterns are then transmitted to the other various brain regions for recognition and identification. This system is unique because, rather than having one receptor for each specific molecule, a variety of different sensory neurons are involved; and each of them recognizes one or more properties of the odor. As a result, a large population of different sensory neurons will respond to a given odor; but each neuron responds differently—thereby giving rise to an odor-specific output response pattern. It is believed that the neuronal circuitry of the olfactory bulb recognizes and identifies this odor-specific output pattern through processing with its circuits.

The concept of employing chemical sensors using pattern recognition systems analogous to those of the mammalian olfactory system has been modestly explored by a number of different research laboratories; and the few detection systems using such an analogous pattern recognition approach today are popularly referred to as "smart sensor systems", or "odor-sensing systems", or "electronic noses". Representative of these research investigations and systems are the following publications: Abe et al., *Anal. Chem. Acta.* 194:1–9 (1987) and 215:155–168 (1988); Carey et al., *Anal. chem.* 58:149–153 (1986), *Anal. Chem.* 58:3077–3084 (1986), *Sens. Actuators* 9:223–224 (1986), *Anal. Chem. 59:1529–1534* (1987); Ema et al., *Sens. Actuators* 18:291–296 (1989); Abe et el., *Anal. Chem. Acta.* 215:155–168 (1988); Stetter et al., *Anal. Chem.* 58:860–866 (1986); Gardner, J. W., *Sens. Actuators B* 4:109–115 (1991); Muller, R. and E. Lang, *Sens. Actuators* 9:39–48 (1986); Muller, R., *Sens. Actuators B* 4:35–39 (1991); Ballantine et el., *Anal. Chem.* 58:3058–3066 (1986); Rose-Pehrrson et el., *Anal. Chem.* 60:2801–2811 (1988); and Grate et al., *Sens. Actuators B* 3:85–111 (1991).

The use of chemical sensors with pattern recognition capabilities have to date taken two non-optical structural formats: the use of surface acoustic wave (SAW) or bulk acoustic wave (BAW) sensors; and the use of piezoelectric sensors. The bulk acoustic wave sensors and surface acoustic wave devices are piezoelectric crystals which have been coated on the external surface with a polymer or a high boiling liquid. BAW and SAW devices are chemical sensors which rely on mass changes, oscillator circuitry and electronic controls to operate the various subsystems and to collect and process the data received. Such detection systems are well described by the following publications: Grate et el., *Anal. Chem.* 65:1868–1881 (1993); Patrash, S. J. and E. T. Zellers, *Anal. Chem.* 65:2055–2066 (1993); Rose-Pehrrson et el., *Anal. Chem.* 60:2801–2811 (1988); Carey et el., *Anal, Chem,* 59:1529–1534 (1987); Zellers et. el., *Sens. Actuators* 12:123–133 (1993); Grate et el., *Anal. Chem.* 60:869–875 (1988); and Grate et al., *Anal. Chem.* 64:610–624 (1992).

In comparison, piezoelectric chemical sensors are quartz crystal electrodes coated with a polymeric film. The use of such piezoelectric sensors to investigate fragrances and the nature of human reactions to different odors is exemplified by Yokoyama, K. and F. Ebisawa, *Anal. Chem*, 65:673–677 (1993).

Insofar as is presently known to date, therefore, while the concept of pattern recognition as an approach for detection of analytes has been explored as a potential alternative to traditional chemical sensors and chemical sensing systems which require one sensor for each analyte or ligand to be detected, all of these prior investigations have been electrically based and rely upon changes in electrical signals as the means for detection and evaluation. In particular, no optical sensor or optical sensing system has ever been envisioned or constructed which would operate to detect multiple spectral responses or evaluate them as spectral recognition patterns. Instead, the conventional guiding principle and requisite axiom of one specifically binding sensor for each analyte or ligand to be detected remains rigidly in force, as demonstrated by the most recent innovations in optical sensors and optical detection systems conventionally. Accordingly, were an optical sensor and detection system developed which would be only semi-selective in its binding and reaction characteristics such that a single dye reagent would provide a variety of different spectral responses for multiple analytes and ligands in a manner which was both accurate and reproducible, such a novel optical innovation and detection system would be recognized as a major pioneering advance and achievement over conventional detection instruments and methods.

SUMMARY OF THE INVENTION

The present invention has multiple aspects, each of which is substantially related to the others. A first aspect of the invention provides an optical sensor for detecting at least one analyte of interest in a fluid sample, said optical sensor comprising:

a supporting substrate; and an array formed of multiple semi-selective sensing receptor units which differ in their constituent chemical formulations, and are immobilized on said supporting substrate for reactive contact with the fluid sample, and react semi-selectively with an analyte of interest, each of said sensing receptor units of said array being comprised of a polymeric substance of conventional chemical composition, and a dye compound of conventional chemical composition which has characteristic spectral properties, and is disposed in admixture with said polymeric substance.

(a) wherein said admixed dye compound absorbs light energy of a predeterminable wavelength and, in the presence of said polymeric substance without an analyte, yields a baseline spectral response which is optically detectable and recognizable as showing an absence of analyte, and (b) wherein said admixed dye compound absorbs light energy of a predeterminable wavelength and, in the presence of said polymeric substance and at least one analyte of interest, generates a modified spectral response which is optically detectable and recognizable as showing the consequence of reaction with an analyte of interest, said sensing receptor units of said array presenting individual and alternative modified spectral responses after semi-selective reaction with an analyte of interest, the overall spectral pattern formed collectively by said alternative modified spectral responses for an analyte of interest resulting in spectral recognition pattern means by which to detect and identify an analyte of interest.

A second aspect of the invention provides an optical sensing apparatus for detecting at least one analyte of interest in a fluid sample, said optical sensing apparatus comprising:

a supporting substrate; and an array formed of multiple semi-selective sensing receptor units which differ in their constituent chemical formulations, and are immobilized on said supporting substrate for reactive contact with the fluid sample, and react semi-selectively with an analyte of interest, each of said sensing receptor units of said array being comprised of a polymeric substance of conventional chemical composition, and a dye compound of conventional chemical composition which has characteristic spectral properties, and is disposed in admixture with said polymeric substance.

(a) wherein said admixed dye compound absorbs light energy of a predeterminable wavelength and, in the presence of said polymeric substance without an analyte, yields a baseline spectral response which is optically detectable and recognizable as showing and absence of analyte, and (b) wherein said admixed dye compound absorbs light energy of a predeterminable wavelength and, in the presence of said polymeric substance and at least one analyte of interest, generates a modified spectral response which is optically detectable and recognizable as showing the consequence of reaction with an analyte to interest, said heterogeneous sensing receptor units of said array presenting individual and alternative modified spectral responses after semi-selective reaction with an analyte of interest, the overall spectral pattern formed collectively by said alternative modified spectral responses for an analyte of interest resulting in spectral recognition pattern means by which to detect and identify an analyte of interest;

means for introducing a fluid sample to said optical sensor for reactive contact;

means for introducing light energy of a predeterminable wavelength to said semi-selective sensing receptor units; and computerized optical detection and evaluation means for optically detecting each alternative modified spectral response generated by said heterogeneous sensing receptor units individually and for evaluating said resulting spectral recognition pattern to determine the presence of an analyte of interest in the fluid sample.

A third aspect of the invention provides an optical method for detecting at least one analyte of interest in a fluid sample, said optical method comprising the steps of:

providing an optical sensor comprised of a supporting substrate; and an array formed of multiple semi-selective sensing receptor units which differ in their constituent chemical formulations, and are immobilized on said supporting substrate for reactive contact with the fluid sample, and react semi-selectively with an analyte of interest, each of said sensing receptor units of said array being comprised of (a) a polymeric substance of conventional chemical composition, and (b) a dye compound of conventional chemical composition which has characteristic spectral properties, and is disposed in admixture with said polymeric substance, (i) wherein said admixed dye compound absorbs light energy of a predeterminable wavelength and, in the presence of said polymeric substance without an analyte, yields a baseline spectral response which is optically detectable and recognizable as showing an absence of analyte, and (ii) wherein said admixed dye compound absorbs light energy of a predeterminable wavelength and, in the presence of said polymeric substance and at least one analyte of interest, generates a modified spectral response which is optically detectable and recognizable as showing the consequence of reaction with an analyte of interest, said heterogeneous sensing receptor units of said array presenting individual and alternative modified spectral responses after semi-selective reaction with an analyte of interest, the overall spectral pattern formed collectively by said alternative modified spectral responses for an analyte of interest resulting in spectral recognition pattern means by which to detect and identify an analyte of interest;

introducing the fluid sample to said optical sensor for reactive contact;

introducing light energy of a predeterminable wavelength to said semi-selective sensing receptor units of said optical sensor;

optically detecting each alternative modified spectral response generated from said sensing receptor units of said optical sensor collectively to form a resulting spectral recognition pattern; and evaluating the resulting spectral recognition pattern using computerized means to determine the presence of an analyte of interest in the fluid sample.

BRIEF DESCRIPTION OF THE DRAWING

The present invention may be more easily and completely understood when taken in conjunction with the accompanying drawing, in which:

FIGS. 11A and 11B are graphs showing alternative modified spectral responses to different chemical compounds generated by a second formulated sensing receptor unit;

FIGS. 12A and 12B are graphs showing alternative modified spectral responses to different chemical compounds generated by a third formulated sensing receptor unit;

FIG. 13 is a graph showing alternative modified spectral responses to different chemical compounds generated by a fourth formulated sensing receptor unit;

FIGS. 14A and 14B are graphs showing the effects of different sequences of chemical reaction upon the alternative modified spectral responses generated by one sensing receptor unit;

FIGS. 15A and 15B are graphs showing the effects of different sequences of chemical reaction upon the alternative modified spectral responses generated another sensing receptor unit;

FIGS. 16A and 16B are graphs illustrating a spectral recognition pattern indicative for air;

FIGS. 17A and 17B are graphs illustrating a spectral recognition pattern indicative for amyl acetate;

DETAILED DESCRIPTION OF THE INVENTION

Figure 1:
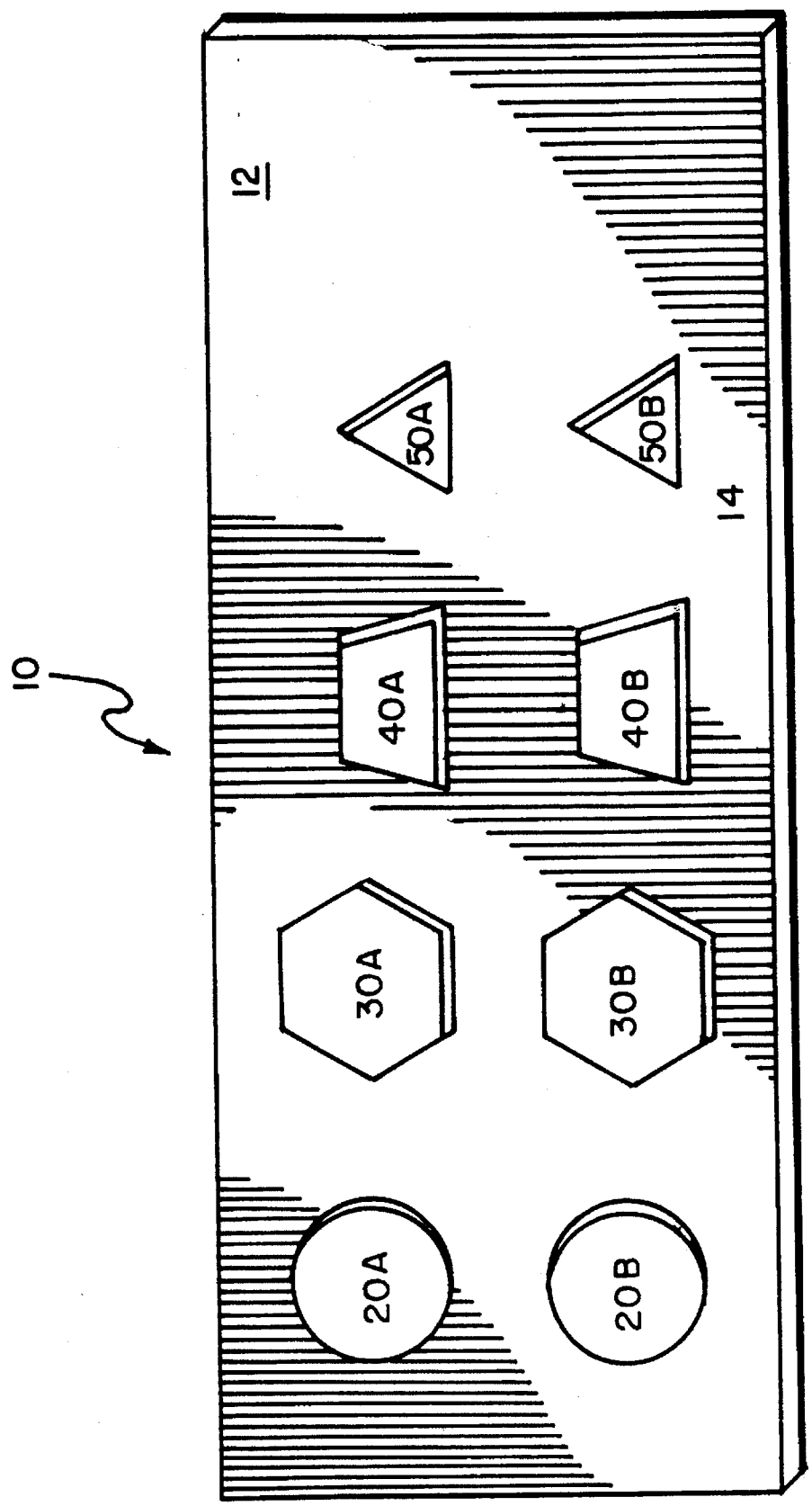
FIG. 1 is a simplified embodiment of the optic sensor comprising part of the present invention.

The present invention is an optical sensor, apparatus, and methodology capable of detecting and identifying one or more analytes or ligands of interest, individually and in mixture, on the basis of spectral response patterns generated by an array of thin film, semi-selective, chemical sensing receptor units. Each formulation of sensing receptor unit comprising the array of the optical sensor reacts with a plurality of different chemical compounds and compositions; and for each individual chemical compound, provides a spectral response pattern over time (by changes in energy intensity, or by changes in wavelength or both of these parameters) which is indicative of the event and consequence of the reaction with a single compound. The array also generates spectral responses and patterns from mixtures of different compounds based upon the optical responses from each of the individual compounds forming this mixture. In this manner, the optical sensor of the present invention mimics the mammalian olfactory system in which multiple receptor neurons react with and respond to the presence of odors by the generation of multiple neural responses concurrently.

The present invention provides an array of thin film, semi-selective sensing receptor units which collectively present multiple spectral responses as a grouped pattern of response progressions which are monitored over time and are evaluated collectively as an assemblage of different spectral responses generated concurrently. The formed collective pattern is then used as the basis for recognition and identification of an analyte or mixture of different analytes.

The present invention therefore represents a radical departure from the conventional approach of optical sensors and detection systems which demand one sensor for each analyte to be detected; and is a singular construction and usage of dye reagents and polymeric materials—each of which is well known, chemically characterized, and commonly available in the laboratory or from commercial sources. As such, the present invention pioneers an entirely unique development both in principle and in construction for the manufacture and usage of optical sensors and optical detection systems; and provides the user with major benefits and unforeseen advantages not previously available heretofore. These include the following.

1. Specific identification of chemical compounds: The present invention can identify specific analytes and mixtures of different ligands by reference to and comparison with previously established spectral recognition patterns for a variety of known chemical compounds and compositions. Conventional chemical detection systems typically discriminate only between different classes of chemical compounds at best (such as organophosphorous and organosulfur classes, polynuclear aromatic compounds, and the like). In comparison, the present invention can identify an analyte of interest as being a specific chemical compound (such as benzene) and has the capacity to be constructed such that the sensors and detection systems of the present invention are capable of discriminating between homologous compounds or ligands (such as detecting and distinguishing between benzene and toluene alone or in admixture).

2. Speed: The optical sensor and detection system uses both temporal and spectral recognition patterns which require only a few seconds of time for a complete response progression to be generated; and require only milliseconds of reaction contact time as the minimal time intervals for detection and identification purposes. As noted and described hereinafter, a complete series of concurrently generated temporal or spectral response progressions can be obtained in twenty seconds or less which collectively form a complete spectral recognition pattern for identification purposes. In comparison, conventionally known sensor systems (including SAW sensors and piezoelectric sensors), typically require several minutes (and often 15 minutes or more), of reaction time in order to accumulate sufficient empirical data to make a determination.

3. Reproducibility of results: The optical sensor and detection systems of the present invention utilize and rely upon recognition and identification of established spectral responses collectively as a pattern which is formed from the signals generated by each thin film sensing receptor unit in the array. Each distinct analyte or ligand of interest (alone or in admixture) coming in contact with the array of multiple sensing receptor units will generate a series of individual spectral responses, repeatedly at each occasion of contact, so long as the chemical constituents of each receptor unit remain unaltered. In this manner, each discrete sensing receptor unit, being a thin film of specified chemical composition and formulation, yields and provides similar spectral responses over time at each occasion repeatedly when that individual analyte or ligand is encountered. Thus, each spectral response progression from identically formulated sensing receptor units will be substantially the same after each encounter with the particular analyte or ligand; and the resulting spectral responses from the different sensing receptor units will collectively form a recognizable group or fingerprint pattern by which to detect and identify that analyte or mixture of ligands routinely and repeatedly.

4. A library reference paradigm: The optical sensing apparatus and methodology relies upon and utilizes a prepared library of reference spectral recognition patterns as the means for evaluating and identifying the analyte or a mixture of ligands in the fluid sample. The reference library of spectral recognition patterns is prepared in advance either by the intended user of the detection system and/or by the manufacture of the instrumentation using a diverse variety of different known chemical compounds. Each of the known chemical compounds or compositions, after reacting with the multiple semi-selective sensing receptor units comprising the array, will generate a plurality of spectral responses over time-which collectively form a spectral pattern of response which is stored in the memory unit of the apparatus as an established pattern unique to that compound and is used for recognition purposes subsequently by the system. The library reference of established collective patterns may therefore be expanded and/or customized to meet the demands or requirements of the user or the specific application circumstances. By intentionally reacting known compounds with the optical sensor and detection system, sets of established spectral response progressions and plotted spectral patterns will be generated which will be compiled and stored as a reference set of patterns by the system. The reference spectral recognition patterns will typically be stored in the memory unit of the instrument; and may be maintained and evaluated mathematically as a set of algorithms unique for that specific analyte or ligand. In this manner, any liquid or gaseous sample believed to contain the analyte or ligand (either alone or in admixture with other compounds) will provide spectral responses and a spectral recognition pattern which can then be compared to the previously established reference patterns and evaluated on this basis to determine the presence or absence of that specific analyte or ligand in the sample.

5. Customization to the needs and use circumstances: The present invention intends and envisions that the optic sensor will provide an array of thin film sensing receptor units whose formulated combinations of dye reagent and polymeric material may be varied to meet a particular application or usage; and optimized for detecting a singular group or specific class of chemical compounds expected to be encountered or released in the intended circumstances. Accordingly, a variety of known compositions and compounds which are deemed unique for or indicative of a physical circumstance or location, a hazardous or toxic problem, a clinical or environmental need, or a singular development setting will be exposed in advance to the detection system for reaction with the array of multiple sensing receptor units of the optical sensor to establish a reference library. In this manner, optical sensors and detection systems can be manufactured to detect and identify specific chemical entities which are envisioned or expected to be present in the test sample. Thus, a single optical system can be used in many different applications such as: to detect pollutants in air, water, and soil; to provide qualitative and quantitative measurement of gases such as carbon dioxide, and oxygen in the blood; to identify polynuclear aromatic compounds released from combustion engines; and to monitor specific compounds or elements present during in-flow processing systems for quality control purposes.

In order to understand and appreciate the different aspects of the present invention more fully, the invention will be disclosed in detail by a series of descriptive sections presented seriatim. These include the array of thin film, semi-selective sensing receptor units comprising the optic sensor; the apparatus and instrumentation for optically identifying and evaluating spectral responses; the range and variety of chemical constituents forming the thin films of each sensing receptor unit; the functions of the polymeric substance and the dye reagent forming each thin film sensing receptor unit; the methodology by which optical detection and evaluation is made; and a series of experiments and empirical data which demonstrate the operability and value of the system as a whole.

I. The Array of Thin Film Semi-Selective Sensing Receptor Units.

The optic sensor for detecting an analyte or ligand of interest (or a mixture of these) in a liquid or gaseous sample comprises two component parts: a supporting substrate; and an array formed of thin film, semi-selective sensing receptor units which are heterogenous in that they differ in their constituent chemical formulations and which are all immobilized on the supporting substrate for reactive contact with the fluid sample. A highly simplified construction and exaggerated view of an optic sensor is shown for clarity of understanding and description by FIG. 1.

The sensor 10 appears in a greatly magnified, highly simplistic format in order that the basic structural component parts and the manner of their interaction may be easily grasped. A substantially rectangular supporting substrate 12 is shown having a substantially planar or flat external surface 14. Disposed upon the external surface 14 are a plurality of thin film sensing receptor units 20, 30, 40, and 50 respectively. More than one sensing receptor unit of the same type (chemical formulation) may be employed; and each type of sensing receptor unit is formulated differently as a thin film and has its own unique combination of a polymeric substance and a dye compound which has well characterized spectral properties. In each receptor unit, the dye compound has been intermixed with the polymeric substance as a thin film; and, in the absence of any analyte or mixture of ligands, is able to absorb light energy of at least one wavelength and will yield a spectral response over time (a progression) which is optically detectable and recognizable.

As shown by FIG. 1, the thin films for each sensing receptor unit 20, 30, 40, and 50 have been intentionally and somewhat artificially drawn to show differences in chemical formulation and constituents by geometrically different configurations. It is for this reason and this reason alone that sensing receptor units 20a and 20b are shaped as circles; sensing receptor units 30a and 30b are configured as hexagons; sensing receptor units 40a and 40b are trapezoids; and sensing receptor units 50a and 50b appear as triangles. In manufacturing tangible embodiments of these different sensing receptor units, however, it will be appreciated and understood that there is no restriction or limitation whatsoever regarding the true configuration, overall surface size, or actual placement of the different sensing receptor units on the supporting substrate. The artificial configurations for the different sensing receptor units shown in FIG. 1 are thus merely illustrative and for the benefit of the reader in order to be distinguish among the different sensing receptor units themselves.

Also merely for illustrative and descriptive purposes herein, the simplest format of differing formulations in dye compound and polymeric substance have been employed. Accordingly, a single dye reagent which is a fluorophore (such as Nile Red) has been combined with four different polymers to form four distinct formulation combinations. Thus sensing receptor units 20a and 20b are identified and employ Nile Red dye with the same first polymeric composition; while sensing receptor units 30a and 30b are identical and employ Nile Red dye with the same second polymeric substance; and sensing receptor units 40a and 40b are identical and utilize the Nile Red dye with the same third polymer; while sensing receptor units 50a and 50b are identical and employ the Nile Red dye reagent with the same fourth polymer. Each combination of Nile Red dye and a different polymeric material forms a unique combination which is present in duplicate units and is chemically different and distinguishable from the other formulated combinations of the adjacent sensing receptor units.

It will be understood and noted that the differing chemical formulations for each of the sensing receptor units 20, 30, 40, and 50 respectively may be formulated quite differently and distinctly such that only one dye compound and only one polymeric substance is used without repetition in any other receptor unit embodiment or its chemical combination. The range, variety, and diversity of dye reagents and polymers available and suitable for use in forming each of the sensing receptor units individually will be described in detail hereinafter.

The supporting substrate 12, although substantially rectangular in shape within FIG. 1, may take any size, configuration, or appearance; may be geometrically regular or irregular; and may be composed of one or any variety of different materials as the use occasion requires or permits. As shown within FIG. 1, the supporting substrate 12 is a translucent or transparent article such that light energy may pass through without being substantially altered or hindered. The supporting substrate 12 thus serves at least as a physical location and a fixed placement for each of the sensing receptor units 20, 30, 40, and 50. This minimum function of the supporting substrate may be achieved in one of two formats: the individual sensing receptor unit may be manufactured and fabricated as a complete thin film entity; and only as a completely formed thin film then be positioned and immobilized onto the external surface 14 of the supporting substrate 12 using a suitable adhesive, sonic welding, or other means of attachment. Alternatively, each of the multitude sensing receptor units may be individually cast and formed in-situ directly on the surface 14 using conventional polymer processing techniques. In such an procedure, the dye compound and the various monomers or copolymers are combined in admixture; and this reaction admixture is polymerized in place directly on the external surface 14 to form the thin film of the sensing receptor unit as a distinct entity. The details of such manufacture and the alternatives of adhesion or in-situ manufacture are described in detail hereinafter.

In addition to using transparent or translucent substrates for fixing and immobilizing the sensing receptor units, it is also possible to employ optical fibers as the supporting substrate. In this case, an optical fiber is coated with a polymer dye combination on the distal tip. Light can be introduced through the fiber and the optical signal generated by interaction of light with the polymer dye combination can return either back through the same fiber and delivered to a detector or the light signal can go directly to a detector after passing through the polymer dye matrix. In one configuration each polymer dye combination is placed on a separate optical fiber. The individual fibers can then be bundled into an array of optical fibers and held mechanically so that the coated tips are presented with the analyte of interest and the detection scheme can be used to simultaneously or concurrently monitor all optical fibers. In an alternative manifestation the individual polymer dye combinations can be disposed on the tip of an imaging fiber array. Spatial resolution of the imaging array enables each sensing region to be monitored separately.

II. The Optical Sensing Apparatus and Instrumentation System.

In order to be effectively employed, the optical sensor illustrated by FIG. 1 is employed with optical apparatus and instrumentation and utilized as a system in order to detect and identify specific analytes or ligands of interest. A generalized and representative optical apparatus and instrumentation system is conventionally available and preferably employed illustrated by FIG. 2.

Sensor measurements may be performed using the apparatus shown schematically in FIG. 2 in the following manner: White light from an excitation source 100 (such as an arc lamp) is collimated; focused by a lens 101; passed through a nm excitation filter 102; and focused on an optic sensor 10 via a 10X microscope objective 104. The optic sensor 10 is held in an xyz-micropositioner 106 which allows for fine focusing. Excitation light is transmitted and illuminates each thin film sensing receptor unit in the array of the sensor which individually fluoresces in proportion to analyte concentration. The returning fluorescence light is reflected 90° by the dichronic filter 103; desirably, but optimally passed through a beam splitter cube 108; filtered at an appropriate emission wavelength by emission filter wheel 110; and then is detected by the CCD camera 120. Radiometric measurements are obtained by monitoring fluorescence while switching between two excitation filters 102 using the emission filter wheel 110. The CCD camera typically contains a photosensitive element and is coupled to an electronic intensifier; which in turn is connected to a computer having a Video Frame Grabber graphic card that digitizes and processes the video image. Visual imaging is achieved by using a CCD video camera to collect the light which is reflected 90° by the beam splitter cube. Illumination for visual imaging purposes is achieved either by rotating the excitation filter wheel to an empty position (using neutral density filters as necessary); or by illuminating the sample and its environs at the distal end of the sensor with an independent light source.

Figure 2:
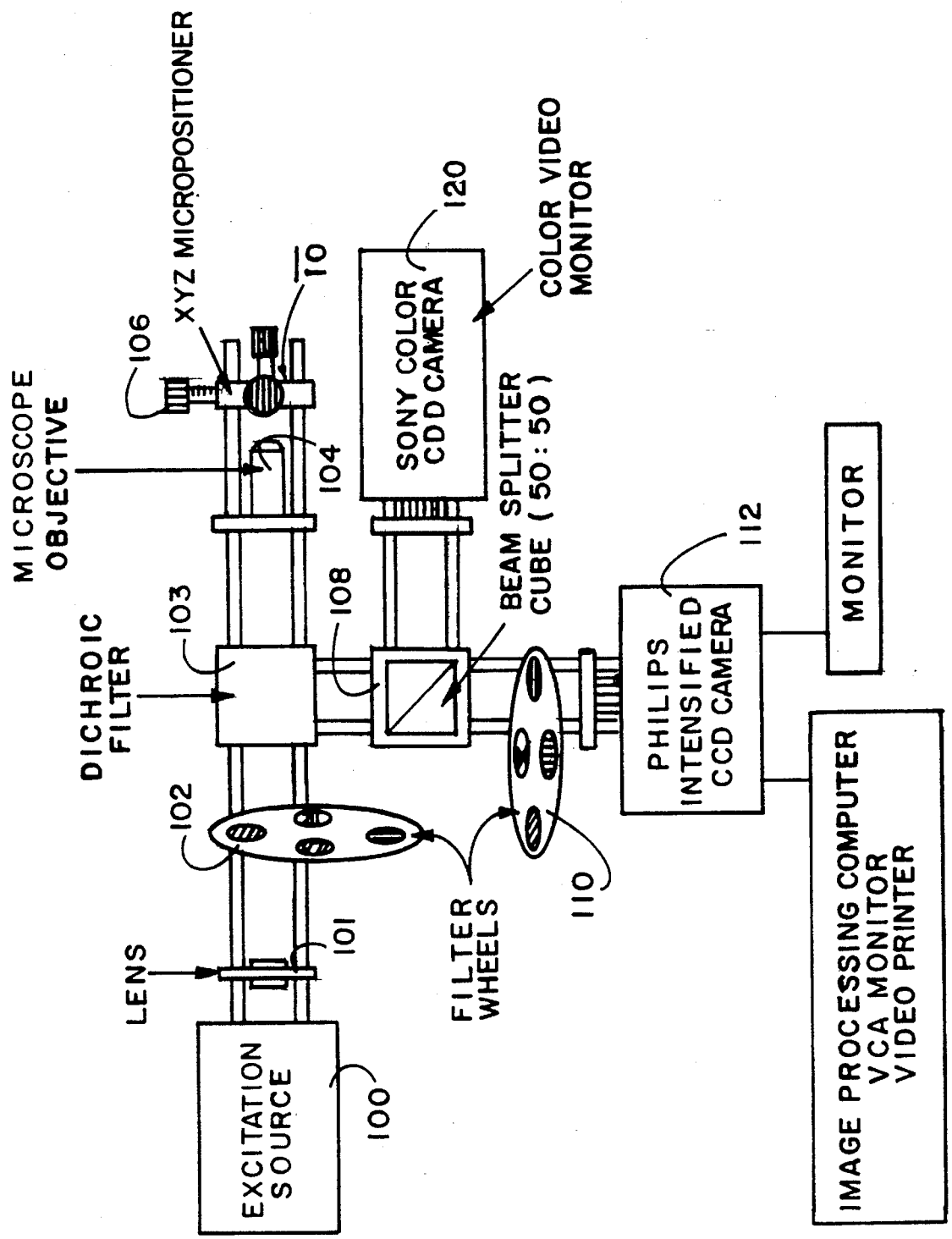
FIG. 2 is an illustration of the optic sensing apparatus and instrumentation of the present invention.

The optic sensing apparatus and instrumentation system shown by FIG. 2 detects changing fluorescence either as changes in light intensity or changes in light wavelength over time-that is, a spectral response progression generated by and released from each individual sensing receptor unit after initial illumination with light energy of a pre-determined wavelength which is then absorbed by the dye compound in each thin film receptor unit. The light energy emitted from each sensing receptor unit individually (in the presence of and in the absence of a ligand or analyte of interest), is collected using a CCD video camera using standard frame grabbing technology and image processing capabilities. Each spectral response progression detected as emission light energy by the detector of the CCD is recorded; and the pattern of fluorescence is shown either as changes in energy wavelength or as different light intensity pixels on the detector representing the spatial dimension. By definition, a pixel is a picture element—a sensitive region—which determines light intensity and/or light energy quantum. In the experiments described and presented hereinafter, each dye compound/polymeric substance combination comprising the thin film of each sensing receptor unit was placed under the objective lens of the epi-illuminating fluorescence microscope; and observed sequences of 33 and 64 milliseconds duration received as video images obtained at 300 millisecond intervals were acquired and placed in the memory of the computer. In this manner, each video sequence showing the light intensity response progressions from each sensing receptor unit lasted about 19 seconds in total.

III. The Spectral Response Progressions and the Collective Response Patterns.

The optic sensor 10, in combination with the apparatus and instrumentation system of FIG. 2, presents an array where each of the sensing receptor units generates a spectral response over time which is detectable and identifiable as a progression of changes in emitted light energy intensity or in emitted light wavelength. Thus, the admixed dye compound of the thin film absorbs exciting light energy of a predeterminable wavelength and, in the presence of the polymeric substance and without any analyte or ligand, yields a baseline spectral response progression over time which is optically detectable and recognizable as showing an absence of analyte. This characteristic result shown as changes in light intensity is illustrated by FIG. 3.

Figure 3A:
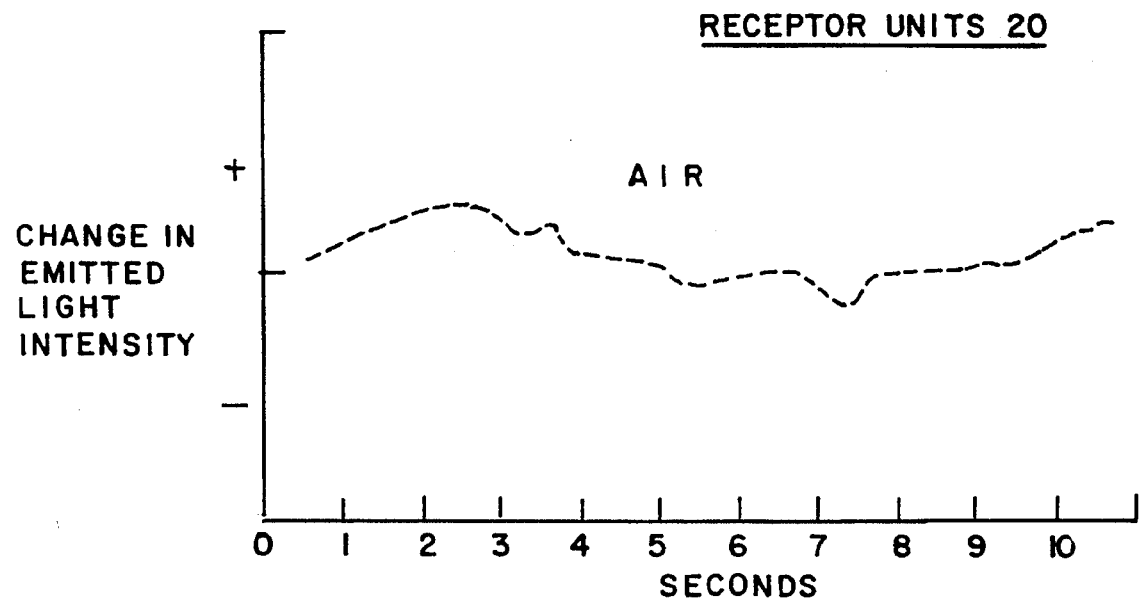
FIG. 3A–3D are graphs illustrating the individual baseline spectral response in air alone generated by the four different thin film, sensing receptor units of FIG. 1.

It will be recalled that there are a pair of identical sensing receptor units 20a and 20b, each of which is a thin film of the same dye compound and polymeric substance in admixture. Each receptor unit 20 will therefore absorb exciting light in the presence of air in the ambient environment; at a substantially constant intensity and then emit fluorescent light as a spectral response. The emitted light energy will not meaningfully fluctuate and change in intensity over time in the presence of air alone (without the presence of any specific analyte or ligand). This is illustrated by FIG. 3A which shows a spectral response progression over approximately 10 seconds duration as an effectively flat or substantially constant plot in which the fluorescence does not change in light intensity to any meaningful degree. The dotted curve of FIG. 3A shows the identical patterns generated by each of the receptor units 20a and 20b cumulatively.

Figure 3B:
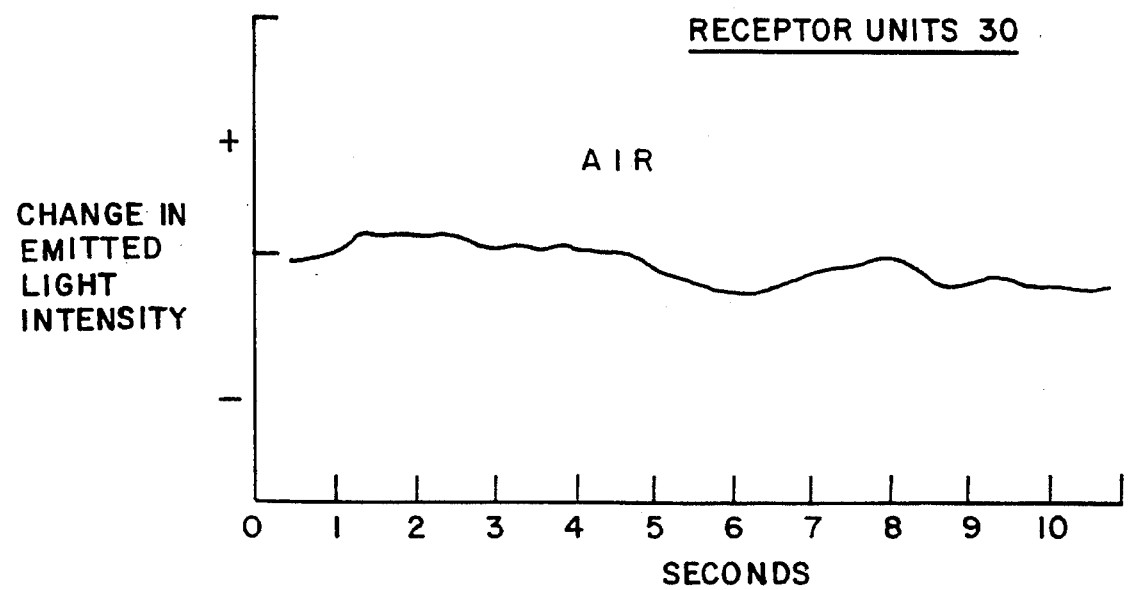
Figure 3C:
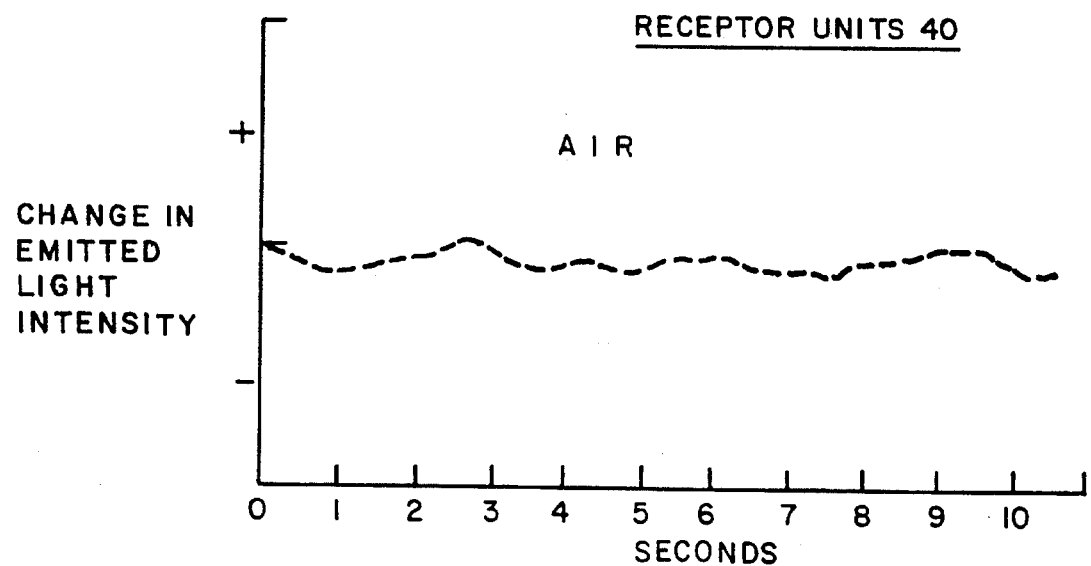

In comparison, sensing receptor units 30a and 30b are identical thin films of a differently formulated combination of dye compound and polymeric substance. When exciting light is introduced to receptor units 30 in air alone, the emissions detected as fluorescent light also do not fluctuate or change over time as illustrated by FIG. 3B. As noted, the plot of spectral response does not meaningfully change over the 10 second duration. FIG. 3*b* represents the progressions of individual responses generated from sensing receptor units 30*a* and 30*b* individually. It is noted and appreciated, however, that the spectral response progression over time generated by receptor units 30 and shown by FIG. 3B is different and distinguishable from that spectral response progression generated by sensing receptor units 20 illustrated by FIG. 3A.

A similar result is revealed as regards sensing receptor units 40 and sensing receptor units 50a and 50b respectively.

Sensing receptor units 40 also differ in their specific formulation of dye compound and polymeric substance forming the thin film of the unit. When illuminated by exciting light energy of a predeterminable wavelength in the presence of air alone, these units yield light emissions which are substantially uniform and constant over time. These are cumulatively shown by FIG. 3C as the spectral response of light intensity over ten seconds duration. However, it will be recognized that the spectral response of light intensity of FIG. 3C does not vary greatly or substantially from either of those shown by FIGS. 3A and 3B respectively.

Figure 3D:
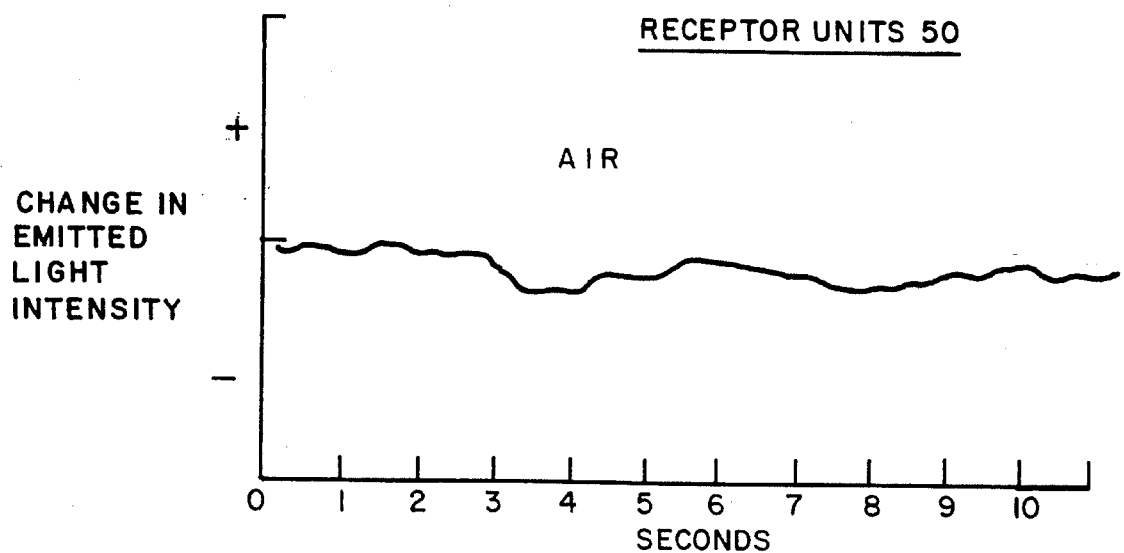

Finally, the spectral response in air alone of the (differently formulated) sensing receptor units 50a and 50b are illustrated by FIG. 3D. This dye compound and polymeric substance formulation differs from those in the other units in the array; and, in the presence of air alone, the introduction of exciting light wavelengths absorbable by the thin films of receptor units 50a and 50b yields a spectral response progression of fluorescent light intensity over time which shows no meaningful changes and fluctuations. The overall spectral response of FIG. 3D, albeit individual, is not markedly different or divergent from those illustrated by FIGS. 3A, 3B, 3C respectively.

Figure 4:
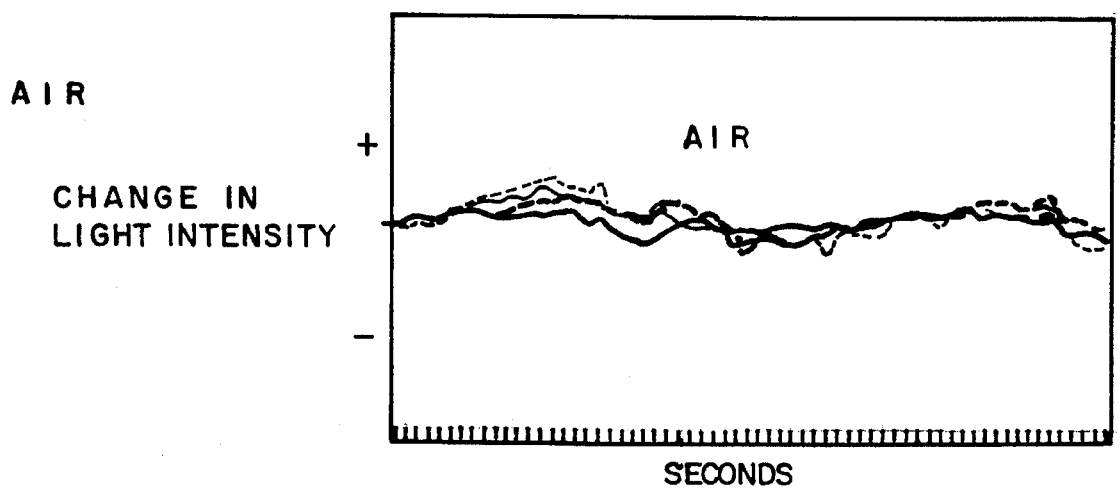
FIG. 4 is a graph showing all the baseline spectral responses of FIGS. 3A–3D collectively as a unified spectral recognition pattern.

The individual spectral response progressions of FIGS. 3A–3D respectively are graphically plotted collectively as a group in FIG. 4. Note that although four distinct plots may be discerned in FIG. 4, all the individual spectral responses generated by the four types of sensing receptor units are effectively alike and substantially uniform. The collective total and cumulative plot of all four spectral response progressions together yield a unique pattern of spectral responses over time—a fingerprint—which recognized as the distinctive collective result and effect caused by the array of heterogeneous sensing receptor units 20, 30, 40, and 50. FIG. 4 thus illustrates a spectral recognition pattern which is indicative and recognizable as a baseline pattern indicative of the presence of any analyte or ligand; and is the distinctive representational total of all the spectral responses from each of the thin film sensing receptor units forming the array. For detection and evaluation purposes, the spectral recognition pattern illustrated by FIG. 4 is stored in the retained memory of the computerized instrumentation and system of FIG. 2; and this initial spectral recognition pattern showing the response progressions serves as the spectral baseline and means for evaluation, as well as for recognizing, and identifying the presence or absence of an analyte or ligand in the testing system.

A very different response and spectral pattern is produced when a first analyte of interest is introduced to the array of semi-selective sensing receptor units of the optical sensor 10. Under these circumstances, the dye compound in each thin film receptor unit absorbs light energy of a predeterminable wavelength and, in the presence of the polymeric substance and the first analyte of interest, generates a first modified spectral response showing changes in light intensity over time which is optically detectable and is the consequence of reaction with the first analyte of interest. This fluctuation in light intensity phenomenon and result is illustrated by FIG. 5 which shows the effect of introducing amyl acetate to each of the sensing receptor units 20, 30, 40, and 50 of the optical sensor 10 illustrated within FIG. 1.

Figure 5A:
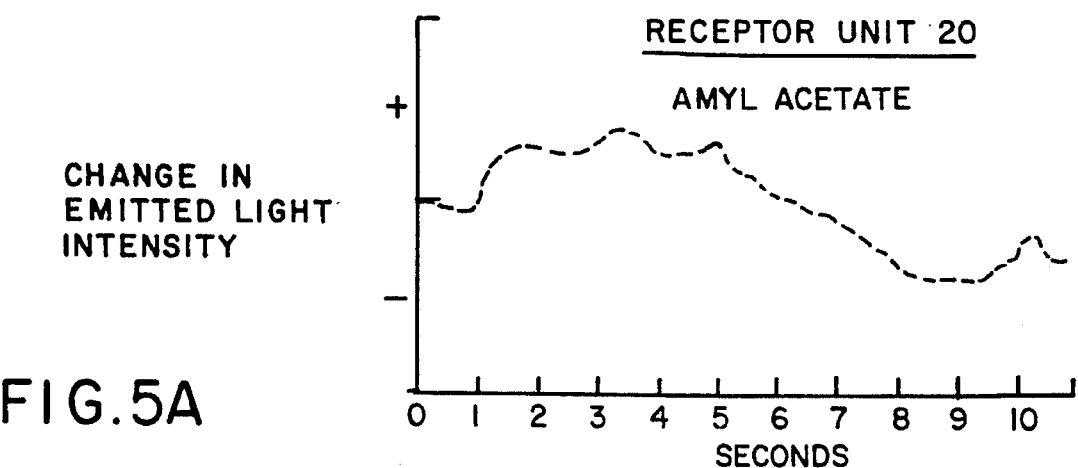
FIGS. 5A–5D are graphs illustrating the first modified spectral response generated by the four different thin film, sensing receptor units of FIG. 1 after reaction with amyl acetate.
Figure 5B:
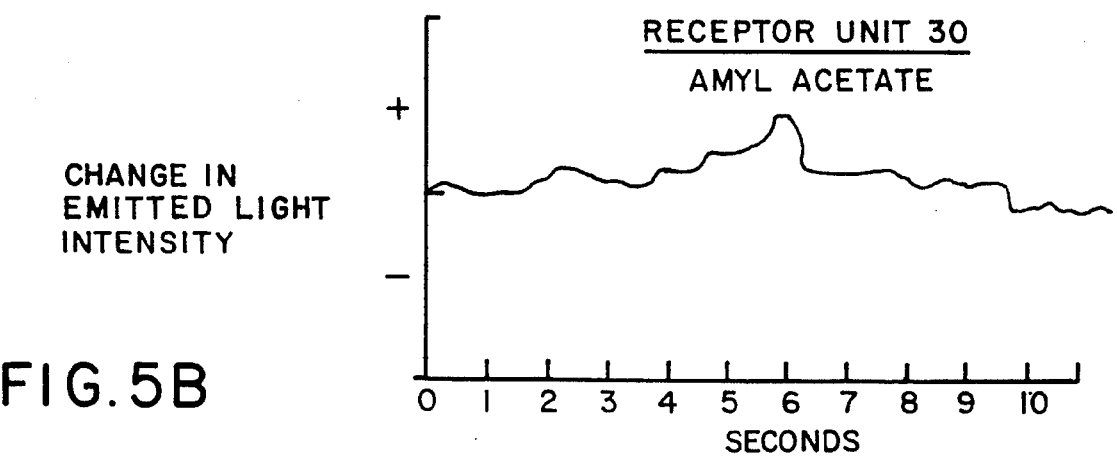

Sensing receptor units 20a and 20b each absorb exciting light energy in the presence of amyl acetate; and the resultant changes in fluorescent light intensity are detectable as major fluctuations over time as shown by FIG. 5A. The spectral response yielded by receptor units 20a and 20b in the presence of the amyl acetate analyte as illustrated by FIG. 5A is remarkably different and distinct from the baseline pattern shown previously by FIG. 3A. The modified light intensity response progression over time is observed and evaluated as being markedly different and unique.

Figure 5C:
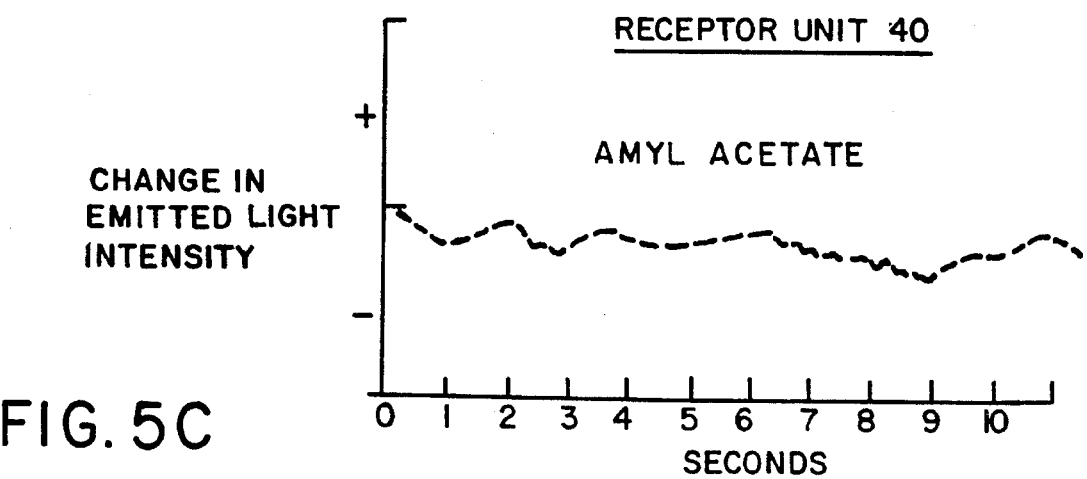
Figure 5D:
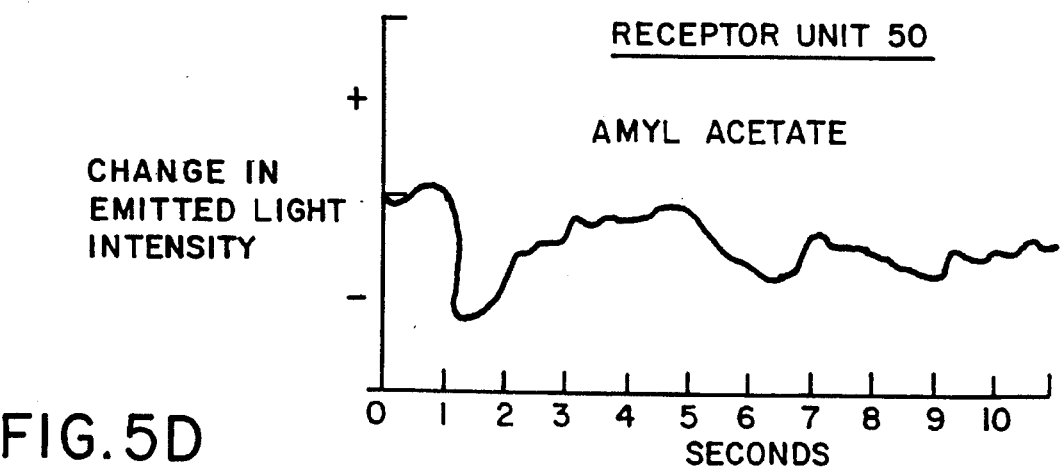

A comparable consequence and result occurs for each of the other sensing receptor units 30, 40, and 50 respectively. A first modified spectral response to the presence of amyl acetate for receptor units 30a and 30b is revealed by FIG. 5B—a response which fluctuates in light intensity and is very different from that baseline response shown by FIG. 3B. Similarly, the first modified spectral response progression over time for receptor units 40a and 40b is illustrated by FIG. 5C; and shows a very different response to the presence of amyl acetate from the baseline progression illustrated by FIG. 3C. Similarly, in the presence of amyl acetate the first modified spectral response over time generated by receptor units 50a and 50b in light intensity over time is shown by FIG. 5D as a substantial variation and fluctuating difference from the baseline spectral response of these sensing receptor units revealed previously by FIG. 3D.

Figure 6:
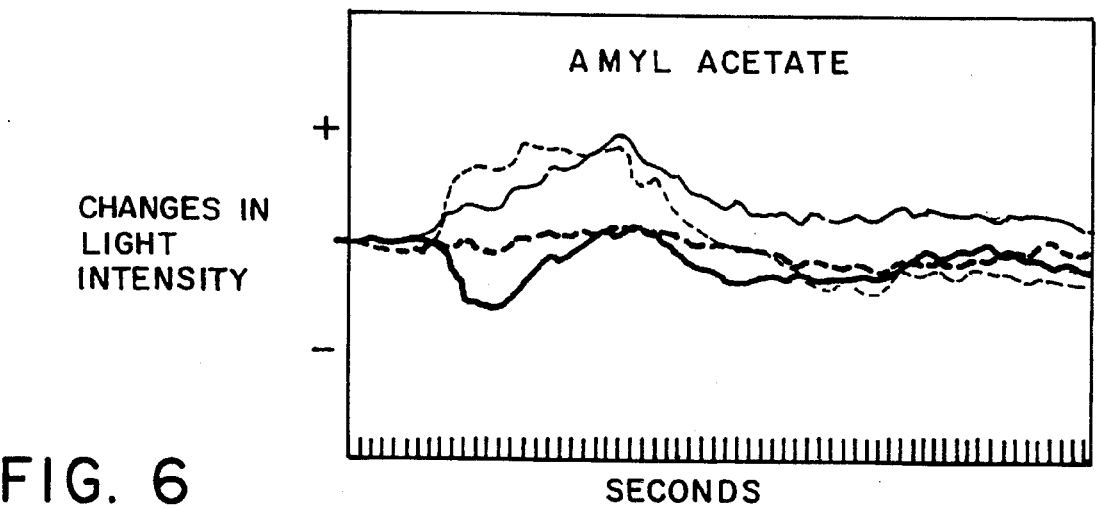
FIG. 6 is a graph showing all the first modified spectral responses of FIGS. 5A–5D collectively as a unified spectral recognition pattern.

The collective total of all four modified spectral response progressions over time from FIGS. 5A–5D together is presented by FIG. 6 as a plotted spectral pattern which is easily recognized as different and distinct from the established baseline pattern shown by FIG. 4. Clearly, the spectral recognition pattern of FIG. 6 as an overall pattern of four plots or progression curves is easily discernible; can be placed in the memory of the computerized instrumentation; and retained as an established recognition pattern and reference which is identifiable as the spectral recognition pattern specific for amyl acetate. Thus, at any time in the future, one may optically detect and identify the presence of amyl acetate in a liquid or gaseous sample easily and quickly by comparing the established spectral pattern of FIG. 6 with the baseline pattern illustrated by FIG. 4. This direct comparison of retained (and established reference) spectral recognition patterns as a baseline (shown by FIG. 4) and for amyl acetate (shown by FIG. 6) allows for accurate, repeated, and speedy detection and identification of amyl acetate using the optical sensor and that specific set of semi-selective sensing receptor units.

The optic sensing apparatus and detection instrumentation system also intends and provides the capability of detecting and identifying multiple analytes or ligands in admixture when introduced together in a liquid or gaseous fluid sample. Using the optical sensor of FIG. 1 and the instrumentation system of FIG. 2, when a second analyte (such as benzene) is introduced to the optical sensor, the overall system operates to provide a second and entirely different result. The admixed dye compound of the thin film in each of the sensing receptor units individually absorbs exciting light energy of a predeterminable wavelength; and, in the presence of the polymeric substance and a second analyte of interest such as benzene, generates a second modified spectral response progression (measurable either as changes in light intensity or as changes in light wavelength over time) which is individually optically detectable and individually recognizable as showing the consequence of reaction with the second analyte of interest, benzene. This is graphically illustrated by FIG. 7.

Figure 7A:
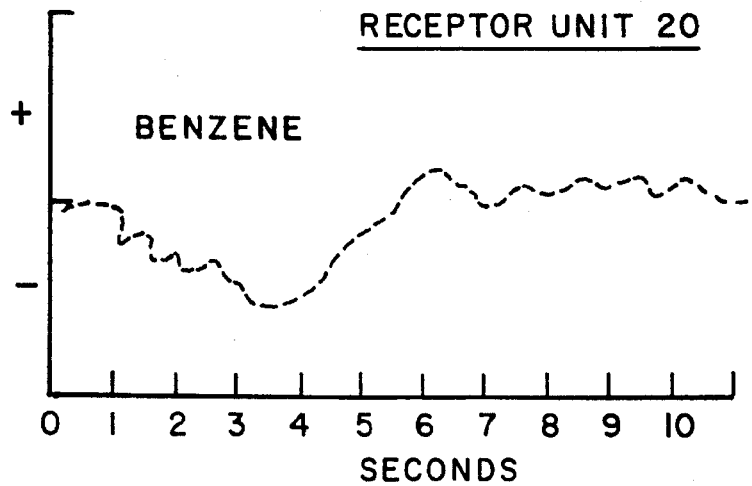
FIGS. 7A–7D are graphs illustrating the second modified spectral response generated by the four thin film sensing receptor units of FIG. 1 after reaction with benzene.

As is shown therein, the sensing receptor units 20a and 20b, in the presence of benzene, absorb exciting light energy and then emit fluorescent light energy which fluctuates and changes in intensity over time and provides a second modified spectrum response progression as shown by FIG. 7A. This second modified spectral response progression of FIG. 7A, the consequence of benzene reaction, is remarkably different and readily distinguishable from that first modified spectral response progression over time for amyl acetate illustrated by FIG. 5A; and is also markedly different and separable from the baseline spectral response illustrated by FIG. 3A. It will be appreciated that in each instance, the same thin film sensing receptor units 20a and 20b were repeatedly employed and utilized. Nevertheless, the same sensing receptor units 20a and 20b yielded three completely different spectral response progressions over time after interaction with air alone, after interaction with amyl acetate, and after interaction with benzene. The semi-selectivity of the sensing receptor units 20a and 20b are thus able to react differently, semi-selectively, and demonstrate a different photokinetic result for each of the three chemical compositions. The sensing receptor units are thus able to generate entirely different spectral responses as a consequence of reaction with each of the three chemical entities.

Figure 7B:
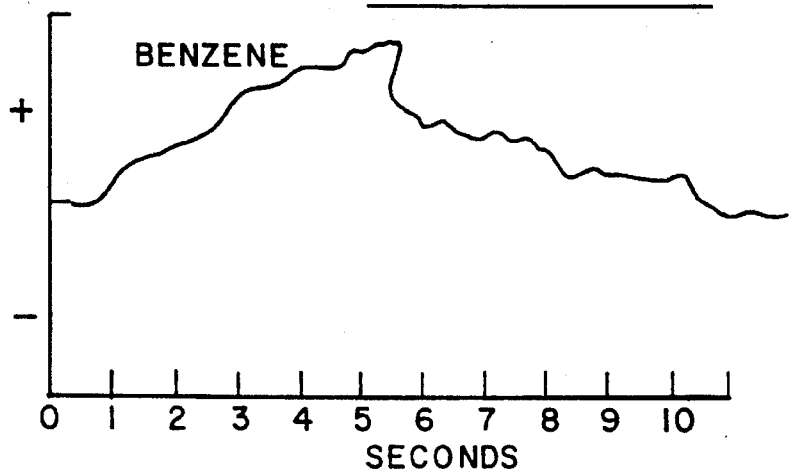
Figure 7C:
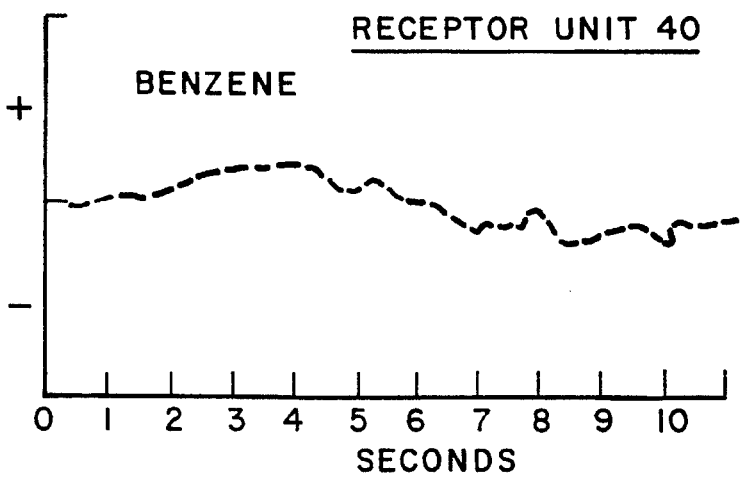
Figure 7D:
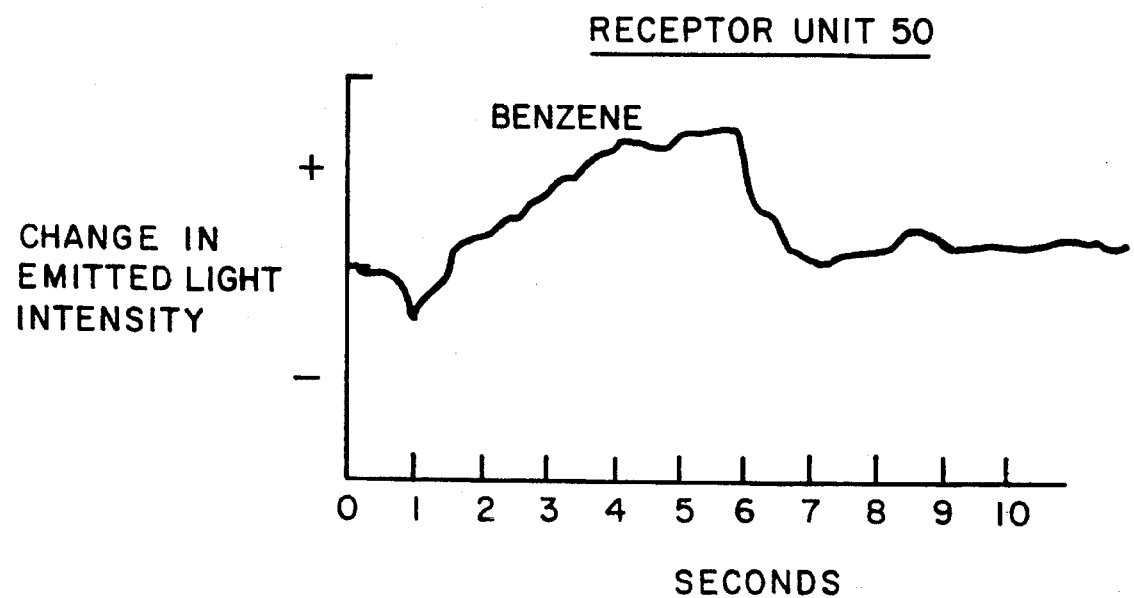

A similar consequence and result occurs for each of the sensing receptor units 30, 40, and 50 respectively. The effect of reaction with benzene by the thin films of receptor units 30a and 30b and the resulting change in light intensity (or light wavelength), the spectral response over time is shown by FIG. 7B—which is markedly different from the first modified spectral response progression yielded for amyl acetate illustrated by FIG. 5B, and is also distinguishable from the baseline spectral response shown by FIG. 3B. The same overall result and consequence of reaction with benzene by receptor units 40a and 40b is illustrated by FIG. 7C; and the consequences of benzene reaction with receptor units 50a and 50b is illustrated by FIG. 7D. In each instance, each of the sensing receptor units show a second modified response over time after reaction with benzene in comparison to the reaction with amyl acetate or the presence of air alone.

Figure 8:
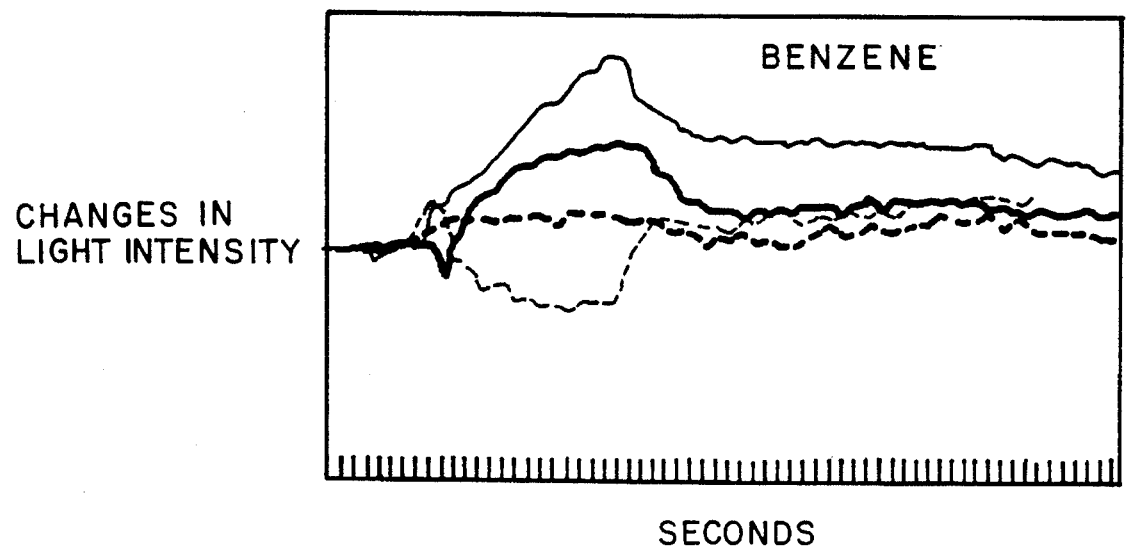
FIG. 8 is a graph showing all the second modified spectral responses of FIGS. 7A–7D collectively as a unified spectral recognition pattern.

The collective sum of all four individual second modified spectral response progressions over time yielded by the entire array of sensing receptor units is illustrated by FIG. 8 as a distinctive group or assemblage pattern. It will be appreciated that the overall pattern formed by all the optical responses plotted over time in the presence of benzene shown by FIG. 8 is easily recognized and quickly distinguishable from that collective group pattern generated for amyl acetate shown by FIG. 6; and is also easily separable and distinguishable from the collective baseline pattern for air alone illustrated by FIG. 4. The group pattern of FIG. 8 generated by the entire array of multiple thin film sensing receptor units collectively is then preferably entered and retained in the memory of the computerized instrumentation and thus becomes part of the established reference library for the instrument and system. In this manner, the library now has retained spectral recognition patterns for three distinct chemical substances (air, amyl acetate, and benzene) using the same optical sensor and instrumentation throughout. Therefore, any fluid sample to be tested subsequently comprising air, or amyl acetate, or benzene alone can be optically detectable and identifiable as individual chemical compounds routinely and reproducibly. Similarly, a fluid sample which comprises a mixture of air, amyl acetate and benzene in combination can also be detected and recognized because the response will contain components of each spectral recognition pattern shown by FIGS. 4, 6, and 8 respectively.

FIGS. 3–8 and the specific entities of air, amyl acetate and benzene respectively will be understood to be merely illustrative examples showing how the essential parts of the system function and representationally disclosing how the multiple spectral responses generated by the array of multiple sensing receptor units are generally employed to form collective group patterns of spectral responses for recognition and identification purposes. Accordingly, these entities embody and demonstrate the underlying principles for practicing the present invention as a whole; and provide only the most basic and fundamental statement and description of the intended range of present invention common to the formats, different modes of operation, and envisioned diversity of applications for the system.

IV. The General Operating and Controlling Parameters of the Invention.

In order to be both effective and efficient as a methodology and instrumentation system able to detect and evaluate one or more analytes or ligands of interest, there are a number of operating parameters and controls which should be followed and incorporated into the system in order to obtain useful or optional results. These include the following:

1. Detectable Entities and Species:

The present invention has the capability to be used in alternative detection modes. For example, conventionally known individual analytes or ligands can be detected and identified as single chemical compounds when present in a liquid or gaseous sample. Alternatively, blends or admixtures of different analytes or ligands in one .fluid sample can also be identified as a mixture of distinct formulated entities or chemical species. In addition, the component compounds of entirely novel chemical compositions and formulations never previously synthesized and/or never characterized may be analyzed to yield detectable features on chemical moiety information using the components of the present invention. This range of system capabilities allows the user to obtain useful chemical information not only about the specific entities and species, but also permit analysis and determination of chemical component parts and moieties of compositions which are themselves entirely novel and unique.

2. The Nature of the Spectral Response:

The present invention intends and permits the user a choice of spectral properties to be employed as the feature for making determination and identifications. The user may, at his option, utilize either light energy intensity or light energy wavelength as the parameter to be detected and measured. Thus, a spectral response over time from a thin film sensing receptor unit can be received as the changes in light intensity over a set time duration; and, alternatively, the spetral response over time to be detected and measured can be the changes in light wavelength over time. If the user so desires, on a very critical analysis if necessary, both forms of spectral response can be performed concurrently, simultaneously, or sequentially.

3. A Preferred Instrumentation.

A preferred apparatus and instrumentation of the optical detection system will utilize a computerized central processing unit and computerized controls for performing the different functions of directing exciting light energy to the correct location; detecting the changes in light intensity and/or light energy wavelengths; and plotting a spectral response progression from each of the thin film sensing receptor units individually. These tasks can be performed concurrently, if not simultaneously, by a computerized network system which not only will collect the raw empirical data as a series of fluctuating fluorescent light emissions but also record and remember them individually in order that the data may appear as recognizable spectral patterns retained for identification and evaluation and stored internally within the reference library set of recognition patterns. The ability to detect, record, and remember the individual spectral response progressions as well as the ability to generate collective patterns and the ability to employ and compare sets of spectral recognition patterns consecutively in series in order to detect and identify specific chemical compounds is best performed in a minimum of time and with maximal efficacy using computerized systems.

4. The Establishment of a Reference Library.

The preferred optical sensing apparatus and instrumentation system requires the development and the presence of a reference library of established spectral recognition patterns for each analyte or ligand which is to be detected by the system. Since the optic sensor provides an array of multiple, semi-selective sensing receptor units—which can be altered markedly in the combinations of dye compound and polymeric substance in admixture-the reference library set of established patterns should reflect the prior test experience and recorded results of using that array of sensing receptor units of specified chemical formulation, Clearly, by altering the chemical constituents (the particular combination of dye reagent and/or polymeric substance in any one or more of the sensing receptor units), the spectral responses over time will be changed; and the previously established spectral recognition patterns associated for known ligands with one established array of sensing receptor units cannot be meaningfully transferred to or be used by another set of differently formulated sensing receptor units. Accordingly, for each array, an established individual reference library desirably should be established which is personal to and unique for the thin film units of that specific optical sensor. Any change in the chemical formulation of any sensing receptor unit will therefore necessitate a change and alteration in the reference library set of established spectral recognition patterns by which identification is made.

5. Detection of Conventionally Known Chemical Entities.

For detecting and identifying well known chemical compounds and species suspected of being present in a liquid or gaseous fluid sample using the present optic sensing apparatus and instrumentation system, the total number of distinct analytes or ligands (alone or in admixture) which can be detected and identified as specific chemical compounds or discrete compositions is limited; and requires that the specific chemical substance have been tested previously and have an established spectral recognition pattern in the reference library set for that particular sensor. Thus, if a fluid sample is introduced to the testing system in which ten different and unrelated chemical compounds are intermixed and, only 5 of these have established spectral recognition patterns within the reference library of the instrument, that system typically will only be able to detect only those 5 particular chemical compounds out of the 10 entities actually present in the sample. Accordingly, it will be recognized that the total number of previously established spectral recognition patterns for known chemical substances is a major factor in that the apparatus; and the system typically cannot detect or identify a distinct chemical entity or species as such which it has not previously encountered and established as a collective pattern spectrally beforehand. The apparatus and instrumentation thus requires preknowledge and a prepared spectral background of collective pattern characteristics before any specific chemical compound or species can be identified. However, once a series of individual spectral responses over time and a spectral recognition pattern is established and stored in the reference library of the instrument, that system will be able to identify and detect the analyte, or ligand or species of interest routinely without error.

6. Range and Diversity of Direction.

As a function and consequence of the freedom to alter, control, and tailor the optic sensor and the array of heterogeneous, semi-selective sensing receptor units in their individual formulated combinations of dye compound and polymeric substance to meet specific use applications and environments, the optical sensing apparatus and instrumentation system can be varied radically and be used in a diverse range of different applications. This range and variety provides the user with the ability to meet the demand of optically detecting and identifying specific classes of chemical compounds or chemical species alone or in mixture. It is therefore expected that various, dedicated optic sensors will be programmed and used for individual purposes and applications; and that the optic sensor will be replaced and substituted by another when the apparatus and instrumentation system is employed for an alternative or very different usage.

V. Analytes Detectable By An Array Of Heterogeneous Sensing Receptor Units.

The range and diversity of analytes or ligands which may be detected and identified, singly or in combination, by the present invention comprises noxious organic and inorganic compounds in liquid or gaseous form which are volatile in nature; toxic and non-toxic gases; environmental pollutants in air, water, and soil; and any matter which can be dispersed, disaggregated, suspended, or otherwise carried in a fluid medium. A representative, but non-exhaustive general listing is given by Table 1 below.

TABLE 1

| Generally Detectable Analytes (Illustrative Listing) | |
|---|---|
| aromatics | thiols |
| benzene | alkyl thiols having from 1–25 carbon atoms |
| toluene | |
| alkylbenzenes | |
| halogenated organic compounds | carboxylic acids |
| methylene chloride | carboxylic acids, saturated and unsaturated, having from 1–25 carbon atoms } |
| chloroethylene | |
| trichloroethylene | |
| bromorcetate | |
| trichloromethane | |
| fluorohexane | |
| chloroform | |
| bromoform | |
| fluoroform | |
| esters | hydrocarbons |
| alkylacetates, alkyl propionates, alkyl butyrates, etc. | all alkanes, alkenes, and alkynes having from 1–25 carbon atoms |
| metallic salts of fatty acids | |
| alcohols and amines | |
| all primary, secondary, and tertiary organic alcohols and amines and homolog series from 1–25 carbons | |
| aldehydes and ketones | |
| formaldehyde | |
| acetaldehyde | |
| methyl ethyl ketone | |

The analytes which may be optimally detected and measured using the present invention individually and collectively often share characteristics and properties in common. A first and frequently found property is that the analyte or ligand have a discernible polarity. Such polarity includes the polarity of bonds caused by two atoms joined by a covalent bond which share electrons unequally as well as the polarity of molecules which occurs when the center of negative charge lies within the molecular structure and thus constitutes a dipole.

A second commonly shared characteristic of the ligand or analyte is that they may be in any fluid state—that is in a gaseous, liquid, or even in a fluid semi-solid state. The majority of analytes or ligands suitable for detection and identification by the present invention are expected to be primarily in the vaporous and liquid physical states—and thus be fluid as a concomitant property of their existence. However, many organic compounds which typically exist as solids may also be detected and identified via the use of solvents and solvent mixtures as these are conventionally known and used in the scientific literature. Organic solvents and aqueous solvents are well known and generally employed in research and industry; and the suspension, dissolution, and/or displacement of a solid chemical compound by an appropriate solvent will prepare and present a fluid sample suitable for evaluation and analysis by the present invention.

A third common property shared among the analytes and ligands is that they be absorbed and at least partially partitioned by the polymeric material of the thin film; and that the absorbed and partitioned analyte or ligand present in the polymeric material layer meaningfully alter or modify the baseline set of spectral properties generated by the interaction of a dye with the polymeric material which exists prior to introduction of the analyte or ligand of interest. This trait and attribute embodies the semi-selective reactivity feature of the thin film sensing receptor units; and provides the different multiple spectral responses which form the collective recognition patterns themselves.

A fourth feature among the membership of organic analytes and ligands is that they are predominantly but not exclusively hydrocarbons. Such compounds are composed primarily of carbon and hydrogen atoms; but often also contain one or more heteroatoms selected from the group consisting of nitrogen, oxygen, sulfur, phosphorous, and halogen atoms. These hydrocarbons, with or without one or more heteroatoms, may be saturated or unsaturated; may take shape as linear, branched, ring, or polycyclic structures; and present formats which include aliphatic, aryl and alkyl aryl structures or combinations of these. Moreover, it is intended and expected that the hydrocarbon molecule as a whole, exclusive of any heteroatoms which may optionally be present, will comprise from 1 to about 25 carbon atoms in total; and that within this range of carbon atoms, with one or more degrees of unsaturation; as linear, branched, and ring entities; and in multiple structural formats will be present.

In general, regardless of the particular molecular weight of the entity which is to be detected using the present invention, any analyte or ligand which can penetrate and be captured by the polymeric material of the thin film sensor (and thus be absorbed and partitioned during its migration) is suitable for detection using the present invention. The differences among the various hydrocarbons and other organic compounds are deemed to be only in the magnitude of their individual effects upon the dye; and in the time required for the sensor to respond spectrally to the presence of the analyte or ligand within the fluid sample.

To demonstrate, a representative but preferred range of hydrocarbons from petroleum sources suitable for detection by the present invention are in the listing of Table 2 provided below.

TABLE 2

Hydrocarbons from Petroleum Sources Suitable for Detection

Aromatics such as benzene, toluene, the xylenes, ethyl benzene, naphthalene, anthracene, phenanthrene, plus their hydrocarbon derivatives;

Alicyclics (saturated cyclics) such as cyclohexane, tetralin, and their hydrocarbon derivatives;

Paraffins (branched and straight chain) such as propane; normal and isobutane; all paraffinic isomers of C5, C6, C7, C8, C9, and C10;

Olefins such as propylene; the butylenes; all olefinic isomers of C5, C6, C7, C8, C9, and C10;

Halogenated hydrocarbons comprising chlorine, bromine, fluorine, or iodine; and Hydrocarbons of up to 25 carbon atoms containing one or more carbonyl groups (—CO) forming aldehydes and ketones.

VI. The Chemical Constituents of the Thin Film Comprising Each Sensing Receptor Unit.

Each semi-selective sensing receptor unit forming the heterogeneous array is a thin film of carefully controlled and limited thickness; is a structure formed by the polymer and dye reagents including dye reagents and monomer mixtures, copolymerized dyes, trapped dyes, and absorbed dyes; and will appear as a discrete film having a thickness ranging from about 0.01–1,000 microns, a thickness of between 1–15 microns being most preferred.

Moreover, the thin films themselves may be either transparent or translucent. Since a thickness of 0.01–1,000 microns is permissible, none of the thin films demonstrate any substantial optical density (i.e., absorbance). Thus, highly colored materials provide thin films which are virtually transparent because of the short optical path lengths involved.

The polymer comprising a thin film typically is a regular geometric form, substantially flat and smooth, and can present some polymer texture or surface irregularity. Alternative physical configurations, however, are envisioned and intended; such alternatives would include physical configurations shaped as hairs, sleeves, wells or cavities, and irregularly shaped embodiments. The flexibility and tensile strength of the thin film may vary markedly and often will depend upon the polymer actually used. These variances are provided and controlled by the user's particular choice of composition from among the conventionally known different polymer compositions; and by selective choice of parameters such as cross-linking concentration, functional group modifications and the like.

A. The Light Energy Absorbing Dyes Generally Useful:

At least one light energy absorbing dye is disposed in admixture with a polymeric substance to form the thin film which is the sensing receptor unit.

Each light energy absorbing dye formulation or composition suitable for use will react semi-selectively with each analyte or ligand of interest which is present either alone or in admixture with other entities. Moreover, each dye will then show evidence of such semi-selective reactive contact by either absorbing and reflecting a portion of the light energy; or, alternatively, by absorbing light energy and then subsequently emitting light energy of a different wavelength in return. Such reflected or emitted light energy is conveyed from the thin film; and such conveyed light will emerge from the array surface for detection and measurement by intensity or by wavelength of light.

The dyes which may be generally employed and disposed individually within the thin film are all conventionally known and often commercially available. The present invention intends that all the commonly useful properties and capabilities of the various classes of light energy absorbing dyes be employed as needed or desired for the specific use or application. Merely illustrative of the many different dyes are those fluorophores and chromophores listed below within Tables 3 and 4 respectively.

TABLE 3

| Compounds | Excitation Wavelength (range or maximum) | Fluorescence emission range (max) |
|---|---|---|
| A. Fluorophores | | |
| Eosin | 520–530 nm | 530–580 nm (550 nm) |
| TRITC-amine | 555 nm | 570–610 nm (590 nm) |
| Quinine | 330–352 nm | 382–450 nm |
| Fluorescein W | 488–496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris, bipyridium) | 460 nm | 580 nm |
| Texas Red Sulfonyl Chloride | 596 nm | 615 nm |
| B-phycoerythrin | 545, 565 nm | 575 nm |
| (Nicotinamide adenine dinucleotide (NADN) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |

TABLE 4

| Chromophores | Range (max) |
|---|---|
| Iron-salicylate complex | 530 nm |
| Indamine dye | 590 nm |
| INT formazon dye | |
| Hopkins-Cole dye | 560 nm |
| Quinone-imine dye | 500 nm |
| $Fe(SCN)^{+2}$ | 460 nm |
| Malachite Green | 620 nm |
| 4-bromo A-23187, | 340 nm |
| Cresol red | 415 nm, acid; 570 nm, base |
| diphenylcarbazone disulphonic acid | 575 nm |
| Chrome bordeaux B | 575 nm |
| Calmagite | 650 nm |
| Ninhydrin dye | 650 nm |

B. The Preferred Polarity-Sensitive or Solvachromic Dye.

Solvachromic dyes, regardless of specific composition and formulation are preferred for use; and are identified and defined in operational terms as a light energy absorbing substance whose absorption and/or emission spectra are sensitive to and altered by the polarity of their surrounding environment-including gaseous, liquid, and/or solid molecules and ions which are temporarily or permanently present in the immediately adjacent spatial volume. The term "solvachromic" is derived from the recognized and long established characteristics of many fluorophores whose fluorescence emission spectra are sensitive to the polarity of the solvents in which they are employed or found. For example, if the emission spectrum of a fluorophore such as ANS (1-anilino-9-naphthalenesulfonyl acid) is examined in different solvents of varying polarity, one finds that the emission spectrum shifts to shorter wavelengths (blue shifts) as the solvent polarity is decreased. Conversely, increasing solvent polarity generally results in shifts of the emission spectrum of the fluorophore to longer wavelengths (red shifts). Red shifts are often, but not always, accompanied by a decrease in the quantum yield or total of photons emitted for the fluorophore being evaluated. This phenomenon, the change in emission spectrum of many fluorophores with respect to different solvents of varying polarity, is well described by the following publications: Joseph R. Lakowicz, *Principles of Fluorescence Spectroscopy*, Chapter 7, Plenum Press, New York, 1983, pp. 187–255; Mataga et al., *Bull. Chem. Soc. Jpn.* 29:465–470 (1956); Bakhishiev, N. G., *Opt. Spectrosc.* 10:379–384 (1961), and *Opt. Spectrosc.* 12:309–313 (1962), and *Opt. Spectrosc.* 13:24–29 (1962); MacGregor, R. B. and G. Weber, *Proc. N.Y. Acad. Sci.* 366:140–154 (1981).

While the best known examples of solvachromic dyes are fluorophores, the membership of this class as a whole includes both absorbers or chromophores as well as fluorescent molecules. The essential property common to each and every member of this class of dyes is that the chosen dye substance changes its spectral properties when exposed to different solvents of varying polarity. For fluorophores, this spectral change can include either a change of emission intensity or a change in the wavelength of the emitted fluorescent light. For an absorber or chromophore dye, the intensity of color may shift either toward the red or the blue end of the spectrum. To determine whether a chosen dye composition is a member of the class defined as a solvachromic dye, the test is solely an empirical one. When the dye is exposed to different organic solvents of varying polarity, the dye changes its color which is empirically observed as a spectral change. Thus, an absorber dye demonstrates a spectral change through its color, either by altering the intensity of the color or by the observation of an actual color change. Alternatively, a fluorescent dye demonstrates its sensitivity to different solvents of varying polarity through changes in either its absorbing exciting light; or by a change in wavelength of the emitted light; or by a change in the intensity of the emitted light.

By this operational definition and the empirical test method through which any person of ordinary skill in this art may identify a chosen dye substance as being a solvachromic dye, it will be recognized and appreciated that the terms "solvachromic" and "polarity-sensitive dye" defines and identifies a dye formulation which is not only sensitive to different solvents of varying polarity, but also to any other organic entity, molecule, or substance which has a discernible,—that is, a demonstrable or determinable polarity. Thus, organic compositions, compounds, and formulations of varying polarity which are not solvents as such are clearly encompassed and included by this term in addition to those compositions which are classically defined as "organic solvents;" and organic solvents constitute merely one group or family within the membership as a whole forming the class of organic analytes having a discernible polarity. In this manner, while it is most convenient to test and evaluate a chosen dye using a plurality of solvents of varying polarity to empirically demonstrate that the chosen dye is spectrally influenced and altered by the polarity of the surrounding environment, any other kind or type or organic molecule may also be employed to demonstrate the spectral sensitivity of the chosen dye-albeit under less convenient and/or more rigorous test conditions.

To demonstrate the range and diversity of the membership comparing the subclass as a whole which constitutes polarity-sensitive or solvachromic dyes, a non-exhaustive listing of representative examples is provided hereinafter by Tables 3 and 4 respectively. Table 5 provides a representative list of polarity-sensitive fluorophores. Correspondingly, Table 6 provides a range of illustrative examples which are polarity-sensitive absorber or chromophoric dyes.

TABLE 5

Polarity-Sensitive Fluorophores.
Phospholipid Fluorophores
N-(7-nitrobenz-2-oxa-1,3-diazol-4-yl) dipalmittcyl-L-a-phosphatidylethanolamine (NBD-PE)
N-(5-fluoresceinthiocarbamoyl) dipalmitoyl-L-a-phosphatidylethanolamine triethylammonium salt (TITC DPPE)
N-(Lissamine rhodamine B sulfonyl) dipalmitoyl-L-a-phosphatidylethanolamine triethylammonium salt (rhodamine DPPE)
N-(Texas Red sulfonyl) diolsoyl-L-a-phosphatidyle-thanolamine triethylammonium salt.
N-(Texas Red Sulfonyl) dipalmitoyl-L-a-phosphatidyle-thanolamine triethylammonium salt (Texas Red DPPE)
3-palmitoyl-2-(1-pyrenedecanoyl)-L-a-phosphatidyl-choline (10-py-PC)
N-(5-dimethylaminonaphthalene-1-sulfonyl) dipalmitoyl-L-a-phosphatidylethanolamine triethylammonium salt
N-(1-pyrenesulfonyl) dipalmitoyl-L-a-phosphatidyle-thanolamine triethylammonium salt
N-(6-(5dimethylaminonaphthalene-1-sulfonyl) amino )-hexanoyldipalmitoyl-L-a-phosphatidylethanolamine triethylammonium salt
N-(biotinoyl) dipalmitoyl-L-a-phosphatidylethanolamine triethylammonium salt
Anionic Fluorophores
cis-parinaric acid
trans-parinaric acid
p-((6-phenyl)-1,3,5-hexatrienyl) benzoic acid (DPH carboxylic acid)
3-(p-(6-phenyl)-1,3,5-hexatrienyl) phenylpropionic acid (CPH propionic acid)
1-pyrenecarboxylic acid
1-pyrenebutanoic acid (pyrenebutyric acid)
1-pyreneonanoic acid
1-pyrenedecanoic acid
1-pyrenedodecanoic acid
1-pyrenebexadecanoic acid
11-((1-pyrenesulfonyl) amino) undecanoic acid
2-(9-anthroyloxy) palmitic acid (2-AP)
2-(9-anthroyloxy) stearic acid (2-AS)
3-(9-anthroyloxy) stearic acid (3-AS)
Table 3— Continued
6-(9-anthroyloxy) stearic acid (6-AS)
7-(9-anthroyloxy) stearic acid (7-AS)
9-(9-anthroyloxy) stearic acid (9-AS)
10-(9-anthroyloxy) stearic acid (10-AS)
11-(9-anthroyloxy) undecanoic acid (11-AU)
12-(9-anthroyloxy) stearic acid (12-AS)
12-(9-anthroyloxy) oleic acid (12-AO)
16-(9-anthroyloxy) palmitic acid (16-AP)
9-anthracenepropionic acid
9-anthracenedodecanoic acid
1-perylenedodecanoic acid
6-(N-(7-nitrobenz-2-oxa-1,3-diazol-4-yl) amino) haxanoic acid (NBD hexanoic acid)
12-(N-methyl)-N-((7 nitrobenz-2-oxa-1,3-diazol-4-yl) amino) dodecanoic acid
12-(N-methyl-N-((7-nitrobenz-2-oxa-1,3-diazol4-yl) amino) octadecanoic acid
12-(N-(7-nitrobenz-2-oxa-1,3-diazol-4-yl) amino)-dodecanoic acid
11-(9-carbazole) undecanoic acid (11-CU)
11-((5-dimethylam inonaphthalene-1-sulfonyl)amino)undecanoic acid
5-(N-dodecanoyl) aminofiuorescein
5-(N-hexadecanoyl) aminofiuorescein
5-(N-octadecanoyl) aminofiuorescein
5-(N-hexadecanoyl) aminoeosin
1-anilinonaphthalene-8-sulfonic acid (1,8-ANS)
2-anilinonaphthalene-6-sulfonic acid (2,6-ANS)
2-(p-toluidinyl) naphthalene-6-sulfonic acid sodium salt (2,6-TNS)
2-(N-methylanilino) naphthalen-6-suifonic acid sodium salt (2,6-MANS)
bi5-ANS (1,1'-bi(4-anilino)naphthalene-5,5'-disulfonic acid, dipotassium salt)
1-pyrenesulfonic acid, sodium salt
2-(N-octadecyl) aminonaphthalene-6-sulfonic acid, sodium salt Table 5—Continued
Cationic Fluorophores
1,1'-dihexadecyloxacarbocyanine, perchlorate (Di-OC$_{16}$(3))
3,3'-diotadecyloxacarboxyanine perchlorate ("DiO", DiOC$_{18}$(3))
1,1'-didodecyl-3,3,3',3'-tetramethylindocarbocyanine, perchlorate (DiIC$_{12}$(3))
1-1'-dihexadecyl-3,3,3',3'-tetramethyolindocarbocyanine perchlorate ( DiIC$_{16}$(3))
1-1'-dioctadecyl-3,3,3',3'-tetramethylindocarbocyanine perchlorate (":DiI", DiIC$_{18}$(3))
1,1'-didocosanyl-3,3,3',3'-tetramethylindocarbocyanine perchlorate (DiIC$_{22}$(3))
1,1'-dioctadenyl-3,3,3',3'-tetramethylindodicarbocyanine perchlorate (DiIC$_{18}$(5))
3,3'-dioctadecylthiacarbocyanine perchlorate (DiSC$_{18}$(3))
octadecyl rhodamine B, chloride salt (R 18)
rhodamine 6G, octadecyl ester, chloride
rhodamine 101, octadecyl ester, chloride
N-4-(4-didecylaminostyryl)-N-methylpyridinium iodide (4-di-10-ASP)
1-(4-trimethylammoniumphenyl)-6-phenyl-1,3,5-hexatriene, p-toluenesulfonate (TMA-DPH)
6-palmitoyl-2-(((2-(trimethyl) ammonium)ethyl)methyl)amino) naphthalene, chloride (PATMAN)
1-pyrenemethyltrimethylammonium iodide
1-pyrenebutyltrimethylammonium bromide
3-(-anthracene) propyl trimethylammonium bromide
Acridine orange-10-dodecyl bromide (dodecyl acridine orange)
acridine orange-10 nonyl bromide (nonyl acridine orange)
Neutral Fluorophores
1,6-diphenyl-1,3,5-hexatriene (DPH)
1-phenyl-6-((4-trifluoromethyl)phenyl)-1,3,5-hexatriene (CF-DPH)
palldium disodium alizarinmonosulfonate (Pd(QS)$_2$)
Nile Red or 9-diethylamino-SH-benxo[]phenoxazine-5-one
6-propionyl-2 -dimethylaminonaphthalene (prodan)

6-dodecanoyl-2-dimethylaminonaphthalene (laurodan)
N-phenyl-11-naphthylamine
1,10-bis-(1-pyrene) decane
1,3-bis-(1-pyrene) propane Table 5—Continued
p-dimethylaminobenzylidenemalononitrile
N-(5-dimethylaminonaphthalene-1-sulfonyl) hexadecylamine
N-(5-dimethylaminonaphthalene-1-sulfonyl) dihexadecylamine
4-(N,N-dihexadecyl) amino-7 nitrobenz-2-oxa=1,3-diazole (NBD dihexadecylamine)
4-(N,N-dioctyl) amino-7-nitrobenz-2-oxa-1,3-diazole (NBD-dioctylamine)
4-(hexadecylamino)-7-nitrobenz-2-oxa-1,3-diazole (NBD hexadecylamine)
1-pyrenecarboxaldehyde
1-pyrenenonanol
7-dimethylamino-4-pentadecylcoumarin
cholesteryl anthracene-9-carboxylate
1-pyrenemethyl 36-hydroxyl-22,23-bisnor-5-cholenate (PMC)
1-pyrenemethyl 38-(cis-9-octadecenoyloxy)-22,23-bisnor-5-cholenate (PMC oleate)
25-(NBD-methylamino)-27-norcholesterol (NBD-MANC)
25-(NBD-methylamino)-27-norcholesteryl oleate (NBD-MANC oleate)
22-(N-(7-nitrobenz-2-oxa-1,3-diazol-4-yl) amino)-23,24-bisnor-5-cholen-38-9yl
22-(N-(7-nitrobenz-2-oxa-1,3-diazol-4-yl) amino)-23,24-bisnor-5-cholen-38-yl linoleate
N-(3-sulfopropyl)-4-(p-didecylaminostyryl) pyridinium, inner salt (DilOAS-PS)
3-(N,N-dimethyl-N-(1-pyrenemethyl) ammonium) propanesulfonate, inner salt
4-(N,N-dimethyl-N-(1-pyrenemethyl) ammonium) butanesulfonate, inner salt
N-e-(5-dimethylaminoaphthalene-1-sulfonyl)-L-lysine (dansyl lysine)
Nile Blue

TABLE 6

Polarity-Sensitive Chromophores
Phospholipid Chromophores
2(3-diphenylhexatrienyl) propanoyl-3-palmitoyl-La-a-phosphatidyl choline (DPH-PC)
N-(6-(biotinoyl) amino hexanoyl) dipalmitoyl-L-a-phosphatidylethanolamine triethyl ammonium salt (biotin-X-DPPE)
N-((4-maleimidylmethyl) cyclohexane-1-carbonyl) dipalmitoyl-L-a-phosphatidylethanolamine triethylammonium salt (MMCC-DPPE)
N-((2-pyridyldithio) propionyl) dipalmitoyl-L-a-phosphatidylethanamine triethylammonium salt
Anionic Chromophores
15-phenylpentadecanoic acid
5-(N-hexadecanoyl) amino fluorescein diacetate The Polymeric Substance:

The thin film forming each semi-selective sensing receptor unit utilizes a polymeric substance to hold and contain the dye reagent. The present invention intends that any of the conventionally known polymers reported in the scientific literature or commercially available from industrial sources be employed, the particular choice, chemical composition, specific formulation and state of preparation being at the discretion of the user.

In this context, two general formats for polymeric substances are known: a fully prepared polymer or copolymer, existing in bulk as a polymerized composition; and those reagent materials such as monomers, co-monomers, cross linkers and the like which are combined into a reaction mixture and then polymerized in-situ by any of the conventionally known techniques to yield a polymeric substance. Either mode of polymeric substance is suitable for use in making the thin film, semi-selective, sensing receptor unit.

A. Pre-Existing Bulk Polymer Material

The first category of polymeric substance requires that the bulk polymer material be soluble in one or a mixture of solvents or be suspendable and carried by one or more solvents. The bulk polymer is dissolved into and by the chosen solvent (such as chloroform or toluene ), sometimes with the addition of heat. A fixed amount of bulk polymer is dissolved in a premeasured aliquot of solvent to yield a predetermined concentration of dispersed polymeric solution. The dye reagent of choice (in liquid form) is then preferably added as a concentrated stock solution to the dissolved polymer to form the admixture. The prepared admixture of dye reagent/polymer is then cast, spin coated, or molded into a thin film having the requisite dimensions; and in a configuration and size (surface area) to meet the intended application. A number of conventionally known techniques are available to achieve the desired result.

A representative listing of previously prepared bulk polymers suitable for use is given by Table 7 and 8. Also, a list of conventionally available solvents for dissolving the bulk polymer prior to admixture with the dye reagent is given by Table 9.

It will be explicitly understood, however, that the lists of Tables 7, 8, and 9 respectively are merely illustrative of those bulk polymers and organic solvents common to the laboratory and easily obtainable from commercial sources. The listings are thus non-inclusive, not exhaustive, and neither limiting or restrictive to the user; and that any other choice of bulk polymer and organic or aqueous solvent(s) may be substituted at will or as dictated by the intended use application.

TABLE 7

Bulk Polymers.
Silicones and Silicon-Containing Polymers:
Polydimerthylsiloxanes
T-structure polymers
Organohydrosiloxane polymers
Polymethylalkylsiloxanes
Fluoroalkylsiloxanes
Aromatic (phenyl containing) siloxanes
Aromatic polymers with functional groups
Aromatic substituted alkyl polysiloxanes
Silicone gums
Polysilanes
Polysilazanes
Polyalkoxysiloxanes-polysilicatse
T-resins and ladder polymers
Silane-modified polymers
Other Polymers:
Polyethylene
Polypropylene
Polymethylmethacrylate
Polystyrene
Polyhydroxyethylmethacrylate
Polyurethanes
Polyvinylchloride Polyvinylidene chloride
Fluorinated Polyolefins
Chlorofluoropolyolefins
Polysubstituted siloxanes
Parafilm
Polyacrylamide
Polyhydroxymethacrylate

TABLE 8

Specific Polymeric Substances.
Poly (2,6-dimethyl-p-phenylene oxide)
Polycaprolactone
Poly (1,4-butylene) adipate
Polyethylene succinate
Phenoxy resin
Polycarbonate
Polysulfone
Polyethylene glycol
Polydimethylsiloxane, trimethylsiloxy terminated
Fluoropolyol
Polyethylenimine
Ethyl cellulose
Polyepichlorohydrin
Poly [bis(cyanoallyl)]-siloxane
Poly (isobutylene)
Polymethylphenyl siloxane
Polyphenyl ether

TABLE 9

Useful Organic Solvents
Acetone;
Chloroform;
Benzene, toluene, phenol and other aromatics;
Alcohols having 1–25 carbon atoms;
Carbon tetrachloride;
Ethers having 2–25 carbon atoms;
Alkanes, alkenes, and alkyenes having from 1–25 carbon atoms;
Thiols having 1–25 carbon atoms;
Organic acids having 1–25 carbon atoms.
Methylene Chloride
Acetone
Ethyl Acetate B. Polymerizable Thin Film Reagent Mixtures.

When forming and depositing the thin film, it is often desirable that the dye formulations be combined with monomer compounds to form a polymerizable reagent mixture. Among the conventional practices, a variety of different polymerization processes are known, including thermal techniques, photoinitiated methods, ionization methods, plasma methods, and electroinitiation procedures. These different methodologies are exemplified by the following publications, the text of each being expressly incorporated by reference herein.

Thermal methods: Graham et al., *J. Org. Chem.* 44:907 (1979); Stickler and Meyerhoff, *Makromal. Chem.* 159:2729 (1978); and Brand et al., *Makromal. Chem.* 181:913 (1980).

Ionization methods: A. Chapiro, *Radiation Chemistry of Polymer Systems* Chapter IV, Wiley-Intersciences, Inc., New York, 1962a; J. E. Wilson, *Radiation Chemistry of Monomers, Polymers, and Plastics,* chapters 1–5, Marcel Dekker, New York, 1974.

Plasma methods: Yasuda, W. and T. S. Hsu, *J. Polym. Sci. Polym., Chem. Ed.* 15:81 (1977); Tibbet et al., *Macromolecules* 10:647 (1977).

Electroinitiation methods: Pistoria, G. and O. Bagnarelli, *J. Polym. Sci. Polym. Chem. Ed.* 17:1001 (1979); Philips et al., *J. Polym. Sci. Polym. Chem. Ed.* 15:1563 (1977); and Odian G., *Principles of Polymerization,* 3rd Edition, Wiley-Interscience, Inc., New York.

One preferred method of thin film preparation and deposition is via the process of thermal polymerization; and employs one or more temperature activated monomer preparations in admixture with one or more prechosen light energy absorbing dyes as a polymerizable formulation [as described in Munkholm et al., *Anal. Chem.* 58:1427 (1986); and Jordan et al, *Anal. Chem.* 59:437 (1987)]. Such monomer preparations typically comprise solutions of several monomers in admixture and a fixed concentration of at least one light energy absorbing dye conjugated to an organic carrier which can be chemically cross-linked. A representative listing of different monomer compositions suitable for preparing a reaction admixture which subsequently can be thermally polymerized are given by Table 10; an illustrative listing of conjugated dyes ready for admixture and photopolymerization is given by Table 10 below.

It will be appreciated that the listings of Table 10 and Table 11 are merely representative of the many different substances which can be usefully employed in admixture with one or more light energy absorbing dyes to form the thin film coating.

TABLE 10

| A. Monomers | |
|---|---|
| Acrylamide | |
| N,N-methylene bis(acrylamide) (crosslinker) | |
| Hydroxyethylmethacrylate | |
| Ethylene glycol dimethacrylate(crosslinker) | |
| Styrene | |
| Vinyl acetate | |
| (N-(3-aminopropyl)methacrylamide Hydrochloride | |
| [Kodak, Inc.] | |
| B. Comonomer with dimethylsiloxane | |
| (Acryloxypropyl)methyl | (15–20%) |
| (Aminopropyl)methyl | (3–5%) |
| (Methacryloxypropyl)methyl | (2–3%) |
| C. T-structure polydimethysiloxanes | |
| Methacryloxypropyl | (25–50%) |
| Vinyl | (50–75%) |

TABLE 11

Conjugated dye
Acryloyl fluorescein
acryloyl rhodamine
acryloyl eosin
phenol red
acryloyl 8-hydroxypyrene 1,3 disulfonic acid
acryloyl seminapthorhodafluor
acryloyl seminapthofluorescein In addition, the scientific and industrial literature provides many alternative preparations and admixtures which are also suitable for use in making the present invention; and the dyes may be incorporated into the thin film by alternative means and techniques such as entrapment, adsorption, electrostatic binding, and the like. Accordingly, all of these conventionally known preparations are considered to be within the scope of the present invention.

VII. The Functions of The Components Comprising Each Thin Film Sensing Receptor Unit.

A. The Function of the Polymeric Substance:

It is essential to understand the nature, variety, and diversity of interactions which occur between the dye reagent and the polymeric substance forming the sensing receptor unit prior to introducing a sample fluid to the sensor for analysis. Generally, there are two characteristics for the polymeric material as it relates to the sensor construction and performance. The first characteristic and function is the primary role of the polymeric material--capturing the organic analyte of interest to be detected. This capture function and capability is performed by absorbing and partitioning the analyte of interest within the substance and thickness of the polymeric material itself. The absorption and partition occurs between the vapor or liquid phase of the fluid sample and the polymeric material forming one component of the sensor construction. The partitioning of the analyte of interest may be similar within the fluid sample and in the polymeric material, that is the concentration of vapor in each of these two phases may be the same; or more likely, one of the two will be enriched in concentration of the analyte relative to the other. Under ideal circumstances, the polymeric material will serve to concentrate the analyte of interest via its superior solubility characteristics relative to the vapor or liquid phase in preferred embodiments of the receptor units comprising the present invention, the polymeric material will concentrate the organic analyte, which in turn, increases the sensitivity and detection limit of the sensor.

The second function and characteristic of the polymeric material, which will not be present to a similar degree in all embodiments of the sensing receptor unit, is the spectral influence exerted by the polymeric material and its ability to alter or modify the spectral characteristics of the dye independent and separate from the spectral influences and consequences caused by the analyte of interest. This second property and characteristic will often vary with the degree of polarity or the non-polarity of the polymeric material as individually chosen for use in constructing the specific embodiment, as well as with the use or non-use of a solvachromic dye reagent. Polarity as such, however, is not the sole property or mechanism by which the dye's spectral properties are mediated or affected. The hydrophobicity/ hydrophilicity of the dye and the polymer together can play major roles; and the solubility characteristics of the chosen dye within the polymeric material can also influence the outcome. Thus, the properties of the polymeric material containing the immobilized dye may or may not itself alone influence and alter the spectral characteristics of the immobilized dye apart from and prior to introduction of an analyte in a fluid sample.

It will be noted, however, that the essential value and circumstance lies in the polymeric material interacting with the dye and thus providing a background or baseline interaction and dye spectral properties against which all other or subsequent optical determinations and measurements are made and compared. As a consequence of the dye being contained, dispersed, or otherwise immobilized within a particular polymeric material, a background or baseline set of spectral properties for the immobilized and contained dye is produced which are the result and consequence of only the interaction between the polymeric material and the dye. It is this baseline or background set of spectral characteristics against which all optical determinations and changes in spectral properties are subsequently made and measured for the detection of an analyte of interest.

Accordingly, when the sensing receptor unit is then placed in contact with a fluid sample believed to contain one or more analytes having or not having an inducible or fixed polarity, the analytes become captured, absorbed, and partioned by the polymeric material and generates marked changes in the spectral properties of the immobilized dye in the sensor. Thus, directly as a result of the analyte's absorption and partitioning by the polymeric layer, the spectral light absorbing and light emitting characteristics of the immobilized dye become changed from its background or baseline plotted standard provided by the effect of the polymeric material alone.

B. The Semi-Selective Reaction Function of the Dye Polymer Reagent.

There is also an essential requirement and function for the dye reagent in combination with the polymer in each embodiment of the sensing receptor unit. The admixed dye and polymer combination must react semi-selectively with the analyte of interest to be detected. The requirement is easily demonstrated and proven empirically for any analyte and dye polymer blending via reactive contact; and the entire series of individual analytes to be identified—whether introduced singly or as a mixture—must generate a different spectral response progression for each analyte as a consequence of reactive contact with that sensing receptor unit. Thus, the original baseline spectral response yielded by the polymer substance and dye reagent becomes the internal standard against which the effects of analyte reactive contact is measured.

In some instances, however, no meaningful modification, alteration, or change from the original baseline plot will be observed after reactive contact; and such empirical observation and result proves an absence of any sensing selectivity (or specificity) of that individual receptor unit and chemical formulation for that particular analyte or ligand. It will be noted and appreciated that not every sensing receptor unit and dye/polymer formulation will or need be responsive to each and every analyte or ligand presented. To the contrary, same analytes may cause one or more receptor units to be quiescent and present baseline signals, while other receptor units actively respond to yield a spectral response pattern. Under these circumstances, that chemical constituent combination of dye reagent and polymeric material may be used to provide a negative response pattern, but the usage should be employed as an extra feature in addition to those dye/polymer formulations which show a positive change in spectral properties.

At the other extreme possibility, two differently formulated sensing receptor units will empirically exhibit substantially similar optical signals, spectral response progressions, a consequence of reactive contact with a single analyte of interest. The substantial similarity merely duplicates the detection value and function of having time or spectral plots of optical response. Thus one of these particular combinations of dye/polymer may be discarded and replaced for purposes of constructing a heterogeneous array.

C. Possible Mechanisms of Sensing Receptor Unit Operation and Function.

The sensing receptor units described herein are not controlled in operation of function by any particular mechanism of action. The spectral changes exhibited by the sensors which may be operative, will include: (1) polarity changes in the polymeric material generated by the analyte of interest which consequently can impart changes in the spectral properties of the dyes, as these dyes are sensitive to polarity; (2) concentration quenching wherein dyes can associate with the analyte and through this association diminish their light intensity, the degree of association being influenced by the presence or absence of the analyte; (3) changes orientational in nature, in which the polymer, in the presence of the analyte, orients the dye in a particular way which creates an environment for changed spectral properties; and (4) swelling in which the distance between dye molecules changes as a function of the volume change in the polymeric material caused by the introduction of the analyte.

VIII. Experiments and Empirical Data

To demonstrate the range and variety of the differently constituted thin films serving as semi-selective sensing receptor units in an array as described above, some illustrative experiments were performed. These experiments and empirical data will serve to merely demonstrate the utility as well as the diversity of the membership comprising the array of sensing receptor units of the present invention. While the experimental design and results are limited, it will be expressly understood that these empirical details do not either restrict or limit the membership of the class in any way. to the contrary, these empirical results and experiments are merely representative of the number, variety, and diversity of novel and unique thin films which can be advantageously prepared and employed in an array and analyzed with the appropriate computational equipment for the detection of an analyte of interest.

Experimental Series 1

Materials and Processing

The fluorescent dye, Nile Red (NR), has properties which make it promising for using as a sensor. The emission (and excitation) spectrum of the dye, is namely dependent on polarity of its micro environment. When there is a change in polarity, e.g. by applying a polar compound, the emission spectrum of the dye shifts and thus gives either an increase or decrease in fluorescence, dependent on the detection wavelength and the initial polarity of the micro environment (= initial position of the emission spectrum). The goal was to see if, by varying the initial environments of the dye by incorporating the dye into different organic polymers, polymer-dye combinations would result which would each respond with a different change in fluorescence unique for a given analyte.

The first step thus consisted of making thin film combinations of the fluorescent dye, Nile Red, using a series of different organic polymers. Then microscope slides with a thin film combination were analyzed for their spectral responses to several known vapored chemical compositions. After having found a heterogeneous set of films which each responded uniquely to the set of known vapor chemical compositions, the next step was to put the different thin films in one optical viewing field, so that the films could be stimulated under the same conditions. To do so, coverslips instead of slides were coated with the thin film combinations and then broken into small pieces. Those small pieces were then glued on a slide with super glue (Dura), which was not fluorescent by itself.

Silanization

In order to create a good adhesion of the hydrophobic film, the slides and coverslips, needed to be silanized. First the slides were cleaned in concentrated sulfuric acid for 15 minutes, after which they were thoroughly rinsed with distilled water and dried with acetone. The, freshly made, silanization solution consisted of 95% EtOH (adjusted to pH 4.5–5.5) with 2% octamethylcyclotetrasiloxane (Petrarch systems) and .was allowed to stand about 5 minutes, but not much more, before using. The slides were then agitated in the solution for about 2 minutes, followed by a brief rinse in 95% EtOH. After drying the slides for 30 minutes @ approximately 60° C., they were ready for use.

Coating of the Slides

In case of the coated slides, all the listed polymers were loaded with 50 µl of Nile Red (NR) stock solution (2 mg NR/ml toluene=6.3 mM). The choice of the polymers was based on simplicity (no polymerization step) and solubility in organic solvents.

The following polymers were tested, followed by the amount used:
1. Dow corning dispersion coating (DOW), 0.6 g
2. Poly (1,4 butylene adipate) (PBA), Aldrich, 0.5 g
3. Poly (ethylene) succinate (PES), Aldrich, 0.5 g
4. Polydimethylsiloxane, trimethylsiloxy terminated (PDMS), Huls Petrarch, 1.0 g
5. Poly (2,6 dimethyl) 1,4 phenylene oxide (PDPO), Aldrich, 0.2 g
6. Poly caprolactone (PC), Aldrich, 0.2 g
7. Poly ethylene glycol 8000 (PEG), Sigma, 0.5 g All polymers were dissolved in chloroform, while heating (oven app. 60° C.), except for DOW and PDMS, which were dissolved in toluene (no heating required).

Each thin film combination was produced by spin coating the slides. The thickness of each thin film was influenced by the rotations per minute and the viscosity of the coating solution. In this case, a relatively high (unable to be exact) spinning rate and low viscosity was used, which resulted in a very thin film. Each of the different thin films dried almost instantaneously. However, the PDMS film never dried and the PEG film cracked; accordingly, these films were excluded from the experiments.

For the thin film of the coverslips, the dye content with each of the polymers was adjusted as necessary so that each thin film combination would have a similar baseline of fluorescence. The adjustments were: PES, 15 µl NR stock; and PC, 25 µl NR stock. The produced thin films were very thin and were estimated to be less than 5 µm in depth. Each thin film combination showed the dye reagent to be regularly distributed in the polymeric substance as a mixture.

Experiment Setup

Figure 9:
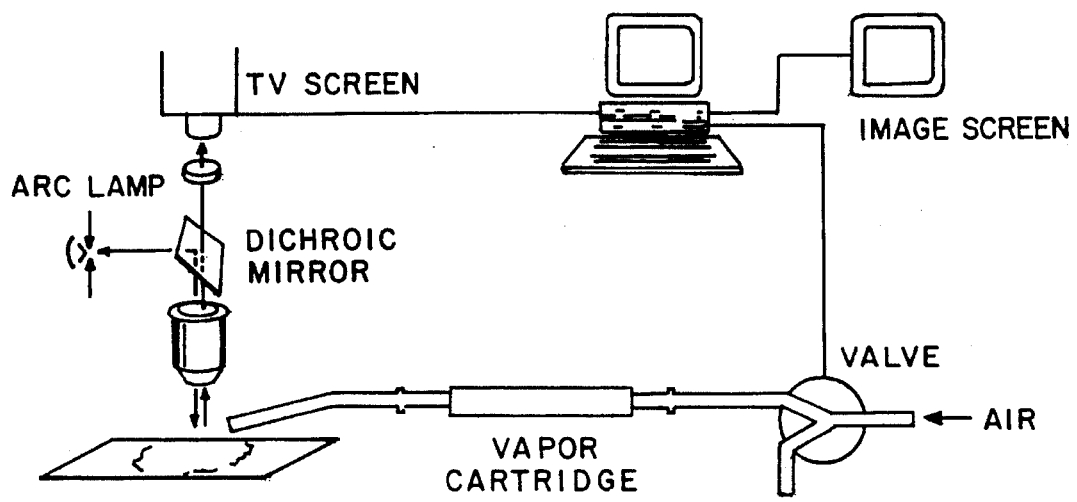
FIG. 9 is an illustration of the instrumentation used experimentally to test gaseous chemical compositions using the present invention.

The experimental instrumentation and apparatus is illustrated by FIG. 9. Using this system, the testing of the sensors is accomplished as follows: Vapors are introduced through a vapor cartridge or they can be introduced directly from a flowing stream of vapor contaminated air. The air stream is introduced to the end of the substrate containing the polymer dye combinations. Air is flowed over the surface for a defined period of time and the spectral response pattern is observed. Air flow is stopped and the sensor returns to its baseline signal. The fluorescence changes are observed by introducing excitation light through a dichroic mirror onto the substrates. The returning fluorescence is then collected through an emission filtering scheme and collected by a two-dimensional detector such as a CCD detector. The resulting intensity images are collected via computer and stored for subsequent signal processing.

Via the experimental setup shown in FIG. 9., the computer, in short, is taking a movie of 64 fluorescence pictures (frames), each representing 33 milliseconds, separated by an 0.3 second interval. During the movie, approximately 19 seconds long, a chemical vapor is puffed on the array for 5 seconds. The change in fluorescence for each thin film sensing receptor unit (Excitation=530 nm, Emission=610 nm) is presented on the screen as a change in the pixel values. The percent change in pixel value as compared to the first frame, was averaged over the entire film in focus and plotted against time.

The following chemical compositions in gaseous form were tested: Air, amyl acetate, benzene, carbon tetrachloride, ethylene dichloride and toluene. To apply the chemical vapor, the airflow (approximately 100 ml/min) was led over a filter paper soaked in the compound (liquid) before the airflow was introduced to the array of thin films.

Evaluations

An initial evaluation of the thin film sensing receptor units was performed using the DOW, PDPO, PC, and PES thin films individually. To demonstrate the semi-selectivity reactivity of each thin film combination, a series of gaseous chemical compounds were individually introduced to each thin film. The spectral responses and the changes in emitted fluorescence (in pixel values) as a function of time progression (as frames per second) are graphically plotted for each thin film sensing receptor unit by FIGS. 10–13 respectively. The DOW thin film semi-selective reactivity is shown by FIGS.: 10A and 10B; the PDPO thin film semi-selective reactors are revealed by FIGS. 11A and 11B; the PC thin film semi-selective reactions are demonstrated by FIGS. 12A and 12B; and the PES thin films' reactions are graphically shown by FIG. 13.

Figure 10A:
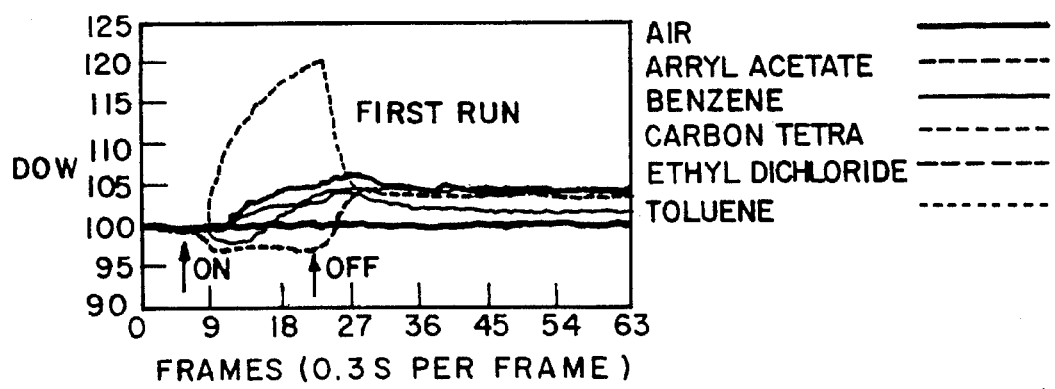
FIG. 10A and 10B are graphs showing alternative modified spectral responses to different chemical compounds generated by a first formulated sensing receptor unit.
Figure 10B:
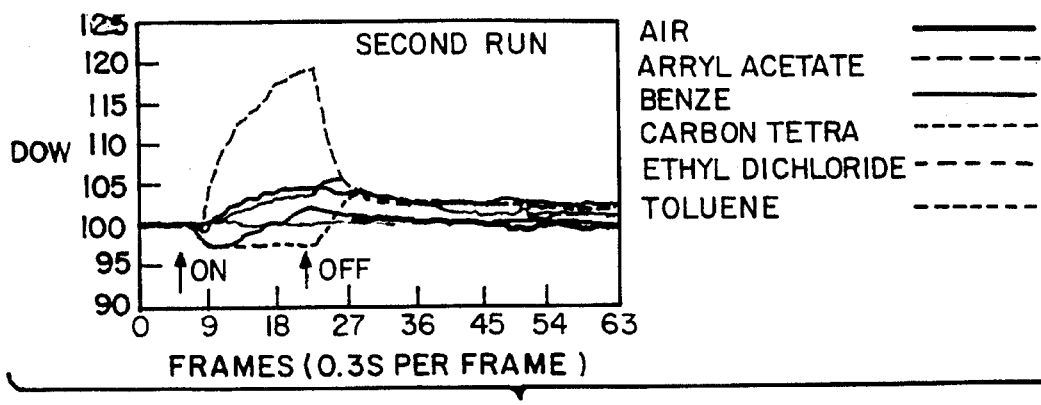
Figure 17B:
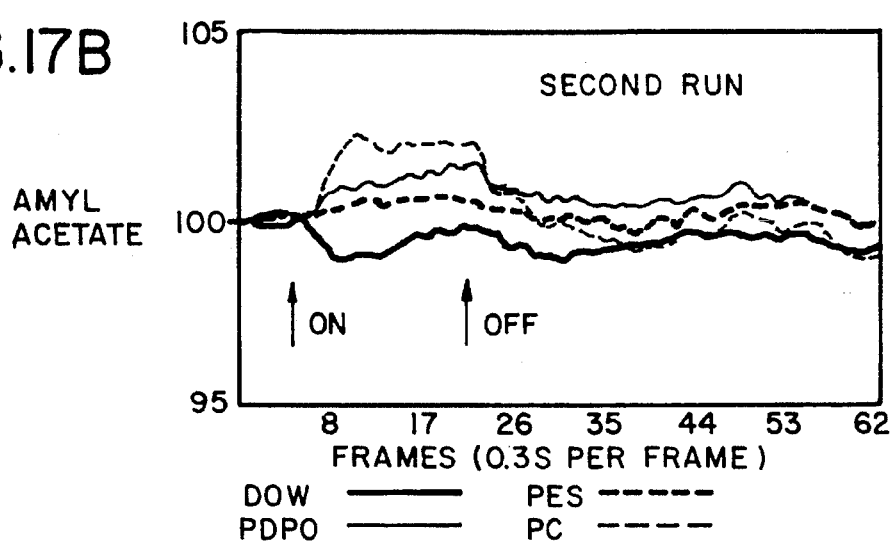
Figure 18A:
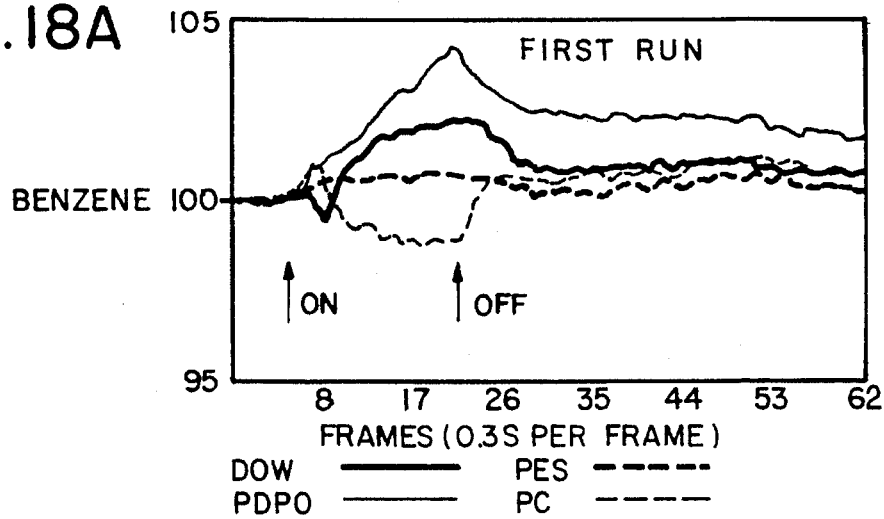
FIGS. 18A and 18B are graphs illustrating a spectral recognition pattern indicative for benzene.
Figure 18B:
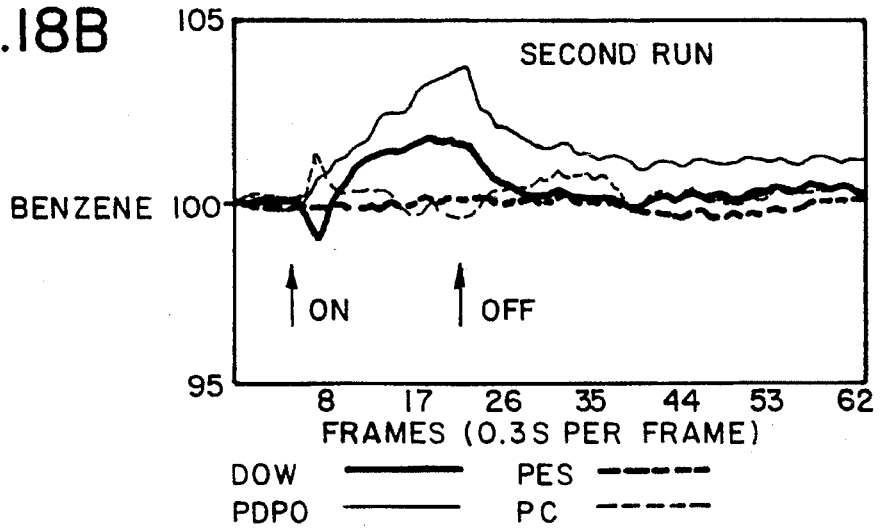
Figure 19A:
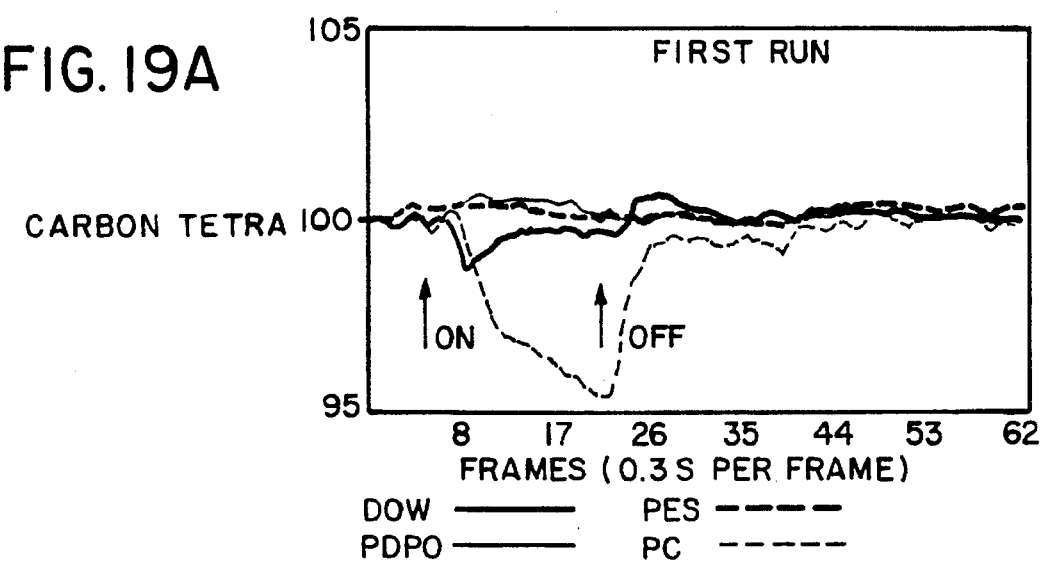
FIGS. 19A and 19B are graphs illustrating a spectral recognition pattern indicative for carbon tetrachloride.
Figure 19B:
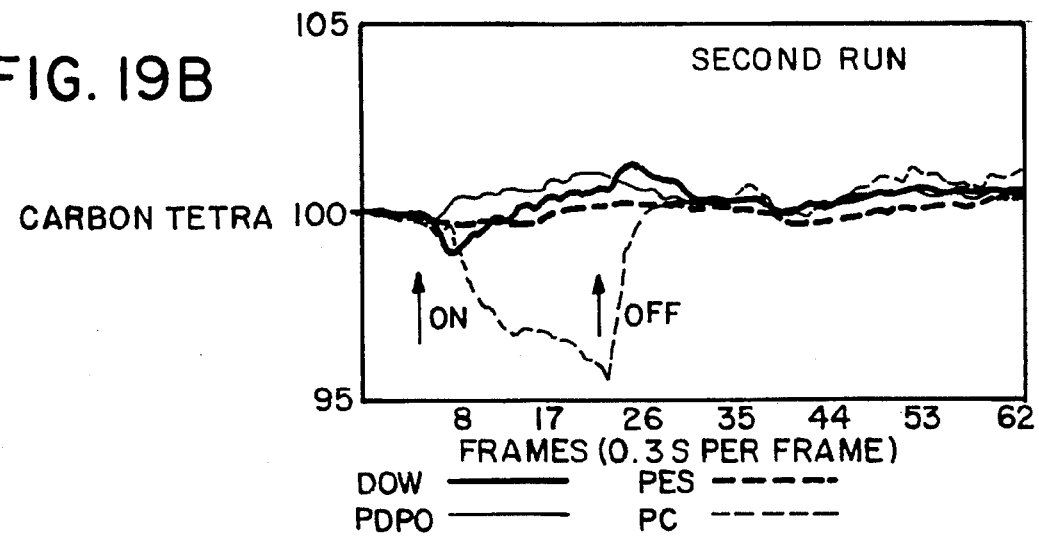
Figure 20A:
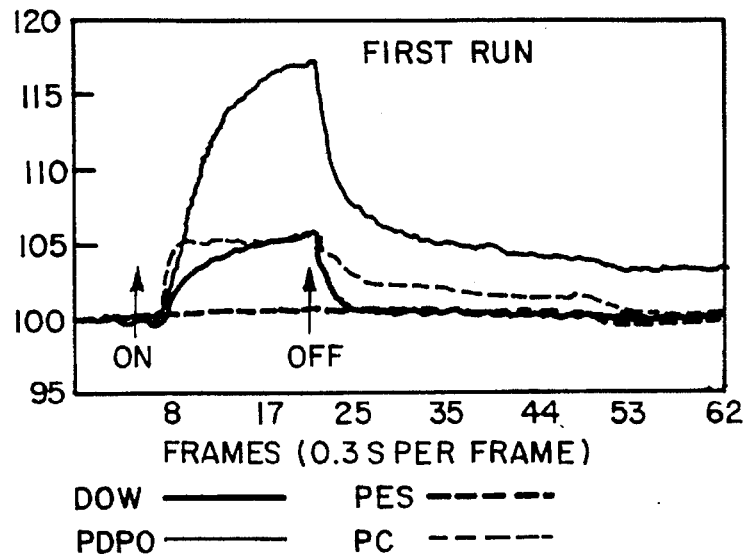
FIGS. 20A and 20B are graphs illustrating a spectral recognition pattern indicative for ethyl dichloride.
Figure 20B:
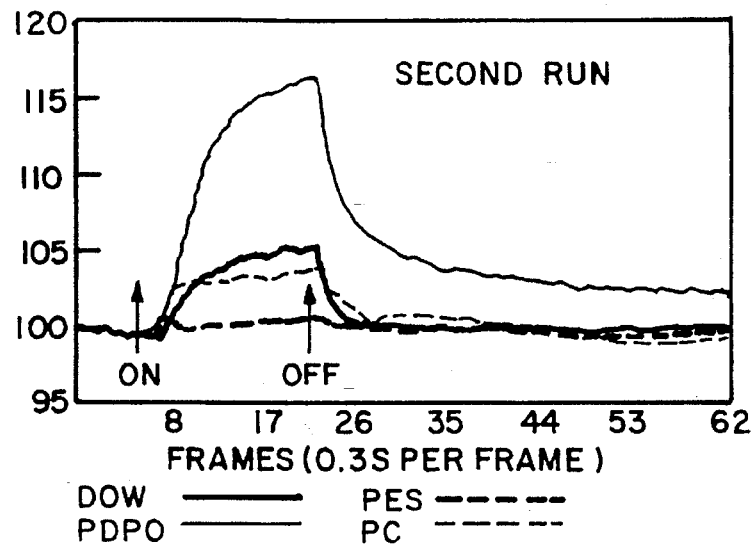
Figure 21A:
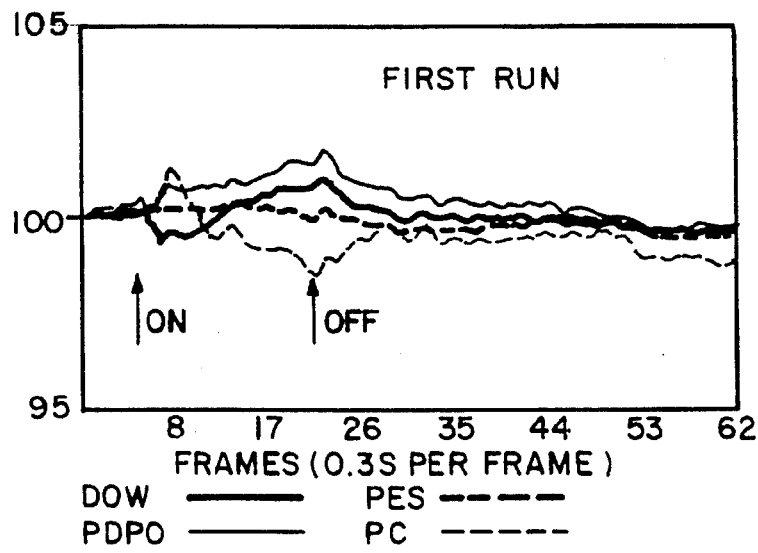
FIGS. 21A and 21B are graphs illustrating a spectral recognition pattern indicative for toluene.
Figure 21B:
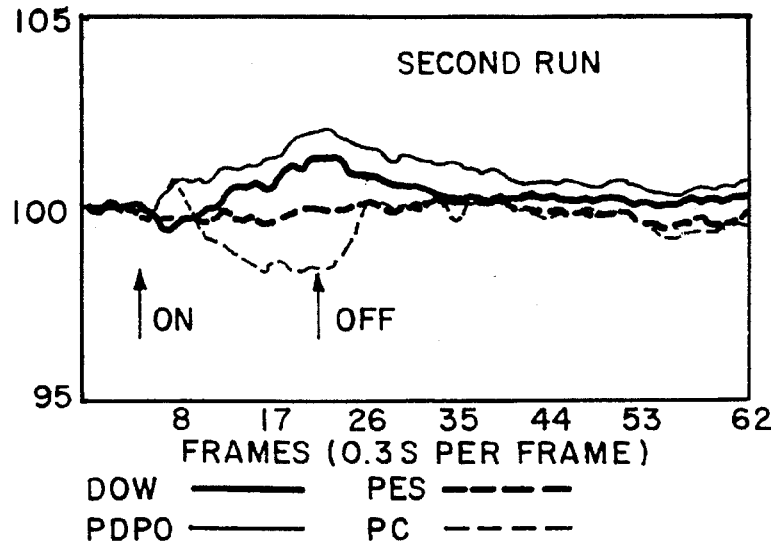

As is shown in FIGS. 10–12, the different thin films on individual slides DOW, PDPO and PC gave unique responses to the tested compounds. Moreover, each thin film sensing response was fast and reproducible. The arrows indicate the on- and off times of the vapor puff. The second run followed directly on the first run, at the same spot on the film and with the different chemical vapors given in the same order: 1 air, 2 amyl acetate, 3 benzene, 4 carbon tetrachloride, 5 ethylene dichloride and 6 toluene. In contrast as shown by FIG. 13, the PES thin film showed no response at all (note the different pixel value scale ), although it did fluoresce intensely. It will be noted and appreciated that the thin film with PBA did respond moderately to most odors, but ethyl dichloride seriously damaged the film. The PBA film was therefore eliminated from any further testing.

To assess if the different chemical vapors influenced each others response, the experiment was then repeated, using PC as the model thin film sensing unit. The order in the second run, however, was altered. As can be seen in FIGS. 14 and 15, the change of order did not introduce major differences. Furthermore, this follow up experiment was performed using another viewing field on the thin film. When the response of PC thin film to the different vapors is compared with that in the prior experiment shown by FIGS. 12A and 12B, one can observe it is nearly identical.

FIGS. 15A and 15B also show the effect of vapor puff duration (1, 2, 3, 4, 5 seconds) on the response. This experiment was also performed on PC thin films using benzene as the gaseous compound. FIG. 15A shows a duration dependent change in spectral response. The order of the different spectral responses as indicated by the legend below the graphs. During the second run shown by FIG. 15B, the PC thin film seemed to fail responding to various chemical vapors after the 2 second puff. The PC thin film was probably exhausted at this stage.

In conclusion from these initial experiments, the four thin films DOW, PDPO, PC and PES were very promising as a heterogeneous sensor array, in that they all give distinct, reproducible spectral response progressions to the tested chemical vapors. The non-responding PES thin film sensing unit is interesting because it can be used as an internal control (e.g. to correct for bleaching and instrument drift).

Experimental Studies

For the subsequent experiments, the individual coverslips holding a thin film dye and polymer combination were broken into small pieces; and the small pieces intermixed as an array in the optical viewer's field. The corrected dye contents of the films turned out to be successful, in that the baseline fluorescences of the four thin films were nearly identical. This arranged setting was tested in the same paradigm as the individually coated slides above; and again the responses of each thin film sensing receptor unit were unique and reproducible. This is demonstrated by FIGS. 16–21 respectively.

Experimentally, it was observed that some thin films bleached during the second trial run (see figures). In our paradigm, the thin films of the array were exposed for 19 seconds to high intensity excitation light. This, plus the used low dye content, is deemed to be the reason for the observed bleaching. Such bleaching can be diminished by using a shutter which only allows light on the preparation for the 33 milliseconds a frame is taken.

Experimental Series 2

Another experimental series was undertaken to demonstrate the feasibility an desirability of using a bundle of optical fiber strands as the substrate for the semi-selective sensing receptor units. Although the quantity of empirical data is limited, the empirical results clearly and unequivocally demonstrate the operability and the utility of an optical fiber based sensor and testing methodology.

Optical Fiber Sensor Array Preparation

The polished proximal ends of nineteen 300 μm-diameter fibers were packed into a stainless steel sheath (1.5"× 0.25"o.d., 0.125"i.d.) and epoxied in a twelve-around-six-around-one-formation, with the fiber tips flush with the end of the sheath. The distal end of each individual fiber was identified and numerically labeled according to its position relative to fiber 1 (arbitrarily selected). The distal ends were then cleaved at even lengths and temporarily bound together (with heat-shrink tubing) for simultaneous polishing. Fibers were polished manually in a four-step process using the following gradient of lapping films: 30, 15, 3, and 0.1 μm. The tubing was removed and the fibers were soaked in concentrated sulfuric acid for two hours to clean.

The bundle was separated into two groups for silanization. The silanizing reagent chosen was based on the nature of the subsequently deposited polymer overcoat. Group I consisted of fibers 2, 4, 6, 8, 10, 12, 13, 15, and 17, while Group 2 contained fibers 1, 3, 5, 7, 9, 11, 14, 16, 18, 19. Group 1 was placed in a 10% solution of (3-trimethoxysilyl) propyl methacrylate 97% in acetone, in the dark, for two hours. The fibers were then rinsed with acetone and cured in the dark for one hour. For silanization of Group 2, a 2% solution of n-octadecyltriethoxy silane in 95% EtOH adjusted to pH 4.5 with acetic acid was prepared and allowed to sit for five minutes. Group 2 was agitated in the 2% solution for two minutes, removed, dipped once in 95% EtOH, and cured at 110 C for 10 minutes.

Polymers

Polymer choices were carried out as follows: fiber 1, PEG(poly ethylene glycol, from Aldrich); fiber 2, PS078.5 (triethoxysilyl modified, polybutadiene (50% in toluene) from United Chemical Technologies, Inc.); fibers 3 and 19, Dow (dimethyl siloxane Dow dispersion coating, from Dow Corning); fibers 4 and 13, PS078.8 (diethoxymethysilyl-modified polybutadiene in toluene, from United Chemical Technologies, Inc. ); fiber 5, blank; fibers 6 and 17, CPS2067 (acryloxypropylmethylcyclosiloxane, from United Chemical Technologies, Inc.); fibers 7 and 18, PC (polycaprolactone, from Aldrich); fibers 8 and 15, PS802 (80–85%) dimethyl (15–20%)-(acryloxypropyl) methylsiloxane copolymer, from United Chemical Technologies, Inc.);

fibers 9 and 14, PBA (poly(1,4-butylene adipate) from Aldrich); fiber 10, PS901.5 (poly(acryloxypropylmethyl siloxane) fibers 11 and 16, PDPO (poly(2,6-dimethyl-1,4-phenylene oxide), from Aldrich); and fiber 12, PS851 ((97–98%)dimethyl(2–3%)-(methacryxypropyl)methyl siloxane Co, from United Chemical Technologies, Inc.).

The two methods used to coat the fiber distal ends were photopolymerization (Group 1) and dip-coating (Group 2). Monomers used in photopolymerization were PS078.5, PS078.8, CPS2067, PS802, PS901.5, and PS851. Dip-coated polymers used were DOW, PEG, PC, PBA, and PDPO.

Photopolymerization

500 µL of polymer was mixed with 400 µL of Kodak Nile Red dye solution (1 mg/mL in dichloromethane) and 5 mg of the initiator benzoin ethyl ether. The steel sheath was then inserted into an X-Y fiber chuck attached to a deposition system comprised of the following components: mercury-xenon lamp, neutral density filter, UV light filter, focusing lens, and pin-hole. The light was focused onto the proximal end of fiber 2 using the ND filter, and the distal end of fiber 2 was isolated. The above polymer/dye solution was drawn up into a capillary tube, dipped onto the distal end of fiber 2, and exposed to 20 µW of 350 nm UV radiation for 30 seconds.

This process was repeated for the remaining fibers in Group 1, with different polymers, amounts of BEE, and lengths of UV exposure time, as listed in Table E1 below.

TABLE E1

| Polymer | Amount of polymer (µL) | Amount of Nile Red (µL) | Amount of BEE (mg) | Dur. of UV exposure(s) |
| --- | --- | --- | --- | --- |
| PS851 | 500 | 400 | 30 | 30 |
| CPS2067 | 500 | 400 | 0 | 10 |
| PS078.5 | 500 | 400 | 5 | 30 |
| PS078.8 | 500 | 400 | 30 | 60 |
| PS901.5 | 500 | 400 | 0.5 | 30 |
| PS802 | 500 | 400 | 30 | 10 |

Dip Coating 0.48 g of poly ethylene glycol (PEG) was dissolved in 2 mL toluene, and mixed with 50 µL of Nile Red solution. Fiber 1 was clamped in a vertical position, distal end facing up. The PEG/Nile Red solution was drawn up into a capillary tube, carefully dipped onto fiber 2, and allowed to dry for one minute. This process was repeated two additional times, resulting in an even layer 70 µm thick.

The same procedure was performed on the remaining fibers of Group 2 with different polymers (as assigned above), and different solvents, as shown by Table E2 below:

TABLE E2

| Polymer | Amt. polym. (g) | Solvent | Amt. solv. (mL) | Nile Red (µL) |
| --- | --- | --- | --- | --- |
| DOW | 0.6244 | toluene | 2 | 50 |
| PEG | 0.48 | chloroform | 1 | 50 |
| PC | 0.19 | chloroform | 2 | 50 |
| PBA | 0.5 | chloroform | 1 | 50 |
| PDPO | 0.2 | chloroform | 1.5 | 50 |

For identity and convenience purposes, especially with respect to FIG. 22 and 24–26, a correlation of optical fiber strands and the corresponding polymer/dye formulated coatings is given by Table E3 below.

TABLE E3

| Optical fiber strand | Polymer/dye identity no. | Optical fiber strand | Polymer/dye identity no. |
| --- | --- | --- | --- |
| f1 | p1 | f10 | p10 |
| f2 | p6 | f11 | p5a |
| f3 | p2a | f12 | p11 |
| f4 | p7a | f13 | p7b |
| f5 | no coating | f14 | p4b |
| f6 | p8a | f15 | p9a |
| f7 | p3b | f16 | p5b |
| f8 | p9b | f17 | p8b |
| f9 | p4a | f18 | p3a |
| | | f19 | p2 |

Figure 22:
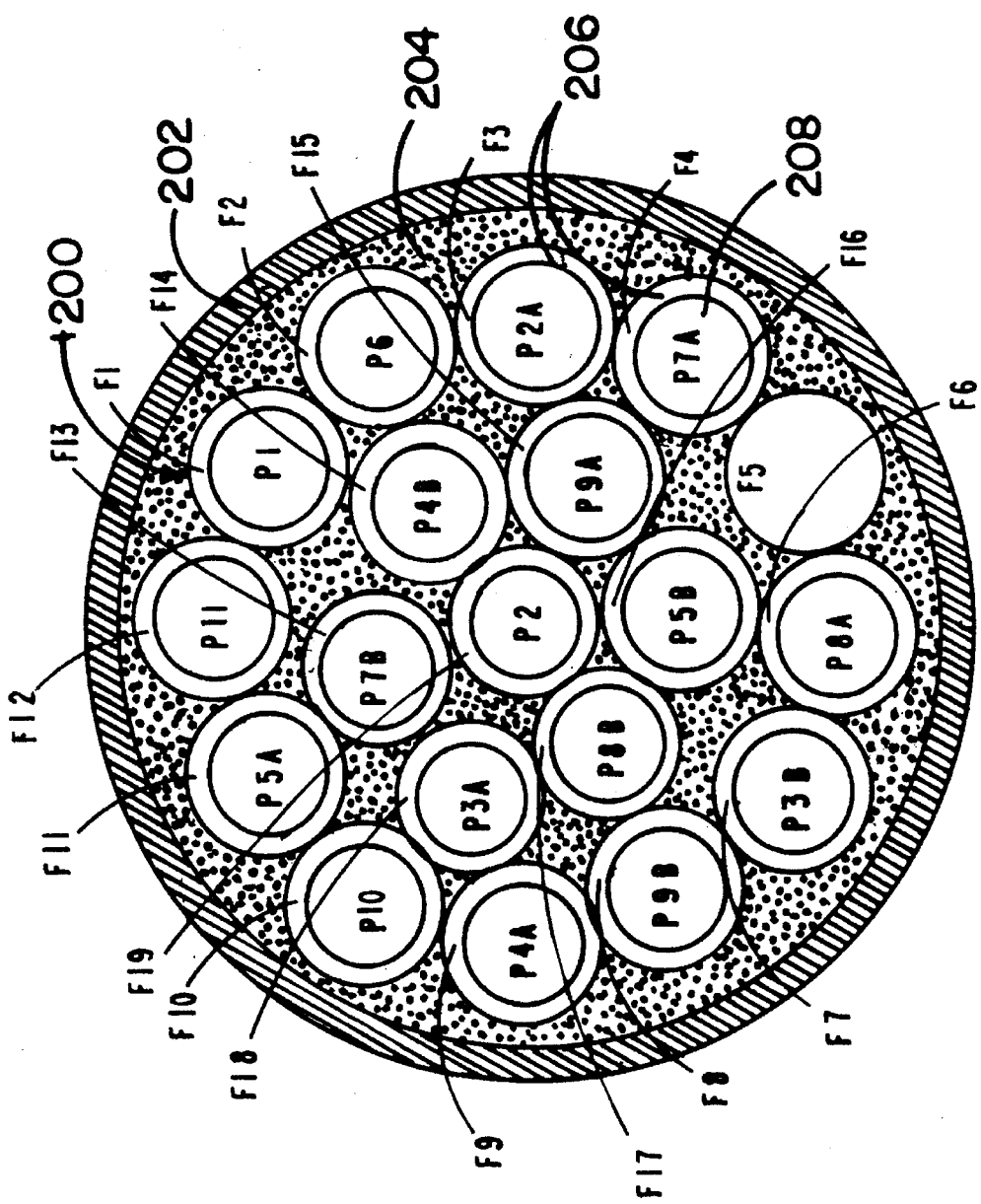
FIG. 22 is an overhead view of a prepared optical fiber sensor, comprising 19 semi-selective sensing receptor units in the array.

The overall result of the photopolymerization and the dip-coating processing is illustrated by FIG. 22 which shows an overhead distal-end view of the prepared sensor comprising individual optical fiber strands (appearing as f1–f19 respectively). The bundle of optical fibers 200 is contained by the epoxy filler 204 within the stainless steel sheath 202. The distal end face 206 of each optical fiber strand (except for fiber 5) is at least partially covered by a polymer/dye film coating 208 formulated as previously described herein. The distal end of this prepared bundle of fibers thus is an array presenting multiple semi-selective sensing receptor units which differ in their constituent chemical formulations and which are immobilized on the distal end faces of the optical fiber strands.

The testing apparatus

Figure 23:
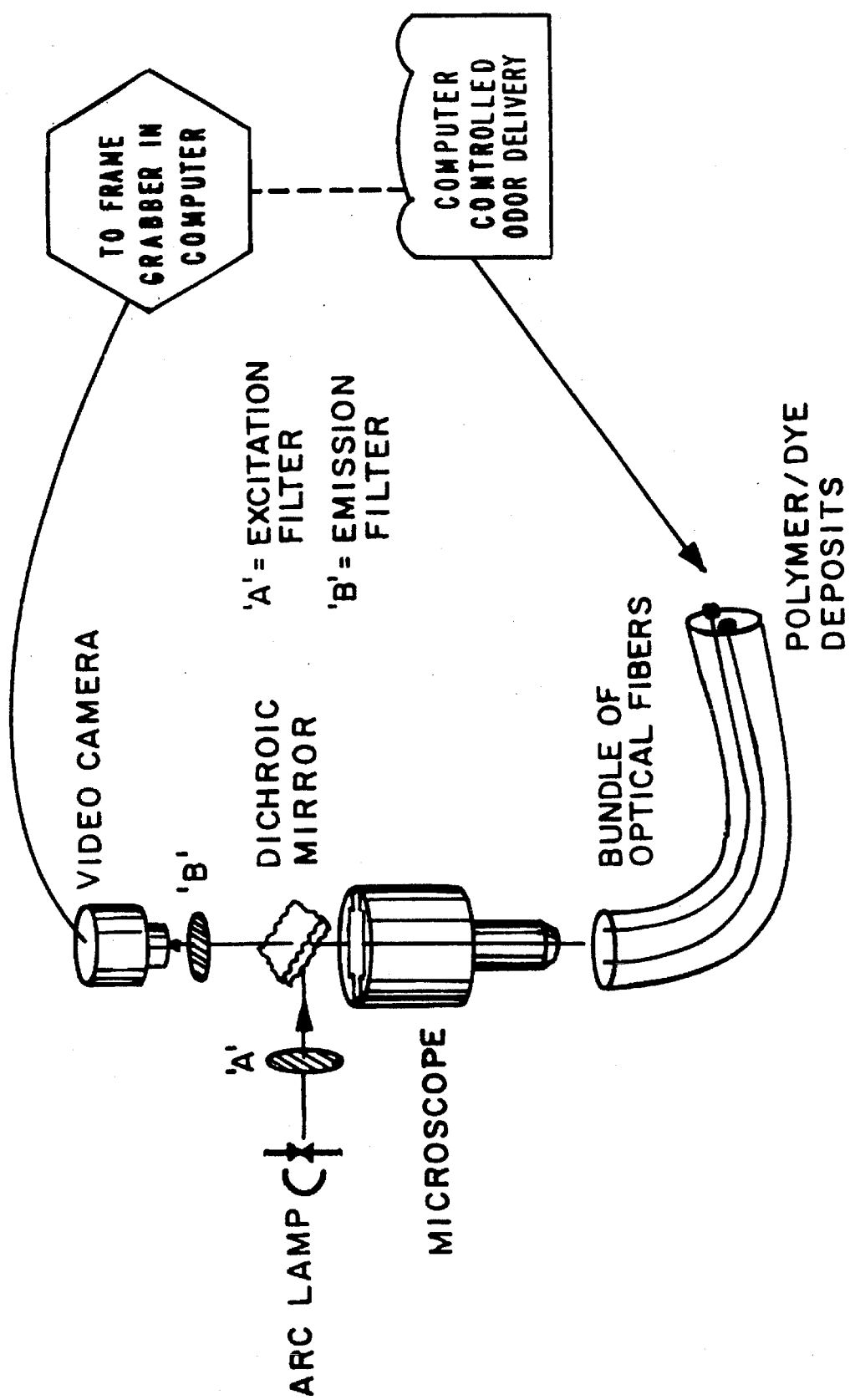
FIG. 23 is an illustration of the instrumentation used experimentally to test vapor samples using the optical fiber sensor array of FIG. 22.

The prepared optical fiber sensor array of FIG. 22, comprised of 18 semi-selective sensing receptor units, is positioned in the test apparatus schematically shown by FIG. 23. It will be recognized and appreciated that the apparatus of FIG. 23 is a variant of those previously shown and described by FIGS. 2 and 9 respectively; and is illustrated in essentially schematic form merely to show the positioning of the fiber optic bundle with respect to the other components of the general testing system and instrumentation already described.

Using the system of FIG. 23, the testing of vapor samples is achieved as follows: Vaporous samples are introduced to the optical fiber sensor via computer controlled delivery means to the distal end of the optical fiber bundle and the individual polymer/dye coated distal end faces forming the array of semi-selective sensing receptor units. Air is initially flowed over the optical fiber array for a defined period of time and the baseline spectral response pattern is observed. The fluorescence changes are generated (using the apparatus of FIG. 23) by introducing excitation light through a dichroic mirror onto the proximal end of the optical fiber bundle. The excitation light is then carried by the individual optical fiber strands to the distal end of the bundle and and excites the 18 thin film coatings of polymer and dye on the distal-end faces of the array in reactive contact with the vapor sample. The fluorescent light emissions from each of the 18 polymer/dye coatings on the distal-end faces of the optical fiber sensor array are then collected through an emission filtering scheme and collected by a two-dimensional detector such as a CCD detector. The resulting intensity images are collected via computer and stored for subsequent signal processing.

Experimental procedure and empirical result

Via the testing setup shown by FIG. 23, a vapor sample containing air and benzene is puffed onto the optical fiber sensor array of sensing receptor units for about 5 seconds. The change in fluorescence from each polymer/dye combination thin film at the end of each optical fiber is presented as a change in pixel values. The percent change in emitted light intensity (as measured in pixel values) for each sensing receptor unit in the optical fiber array over time (as measured in frames) is plotted graphically and is shown by FIGS. 24, 25, and 26 respectively.

Figure 24:
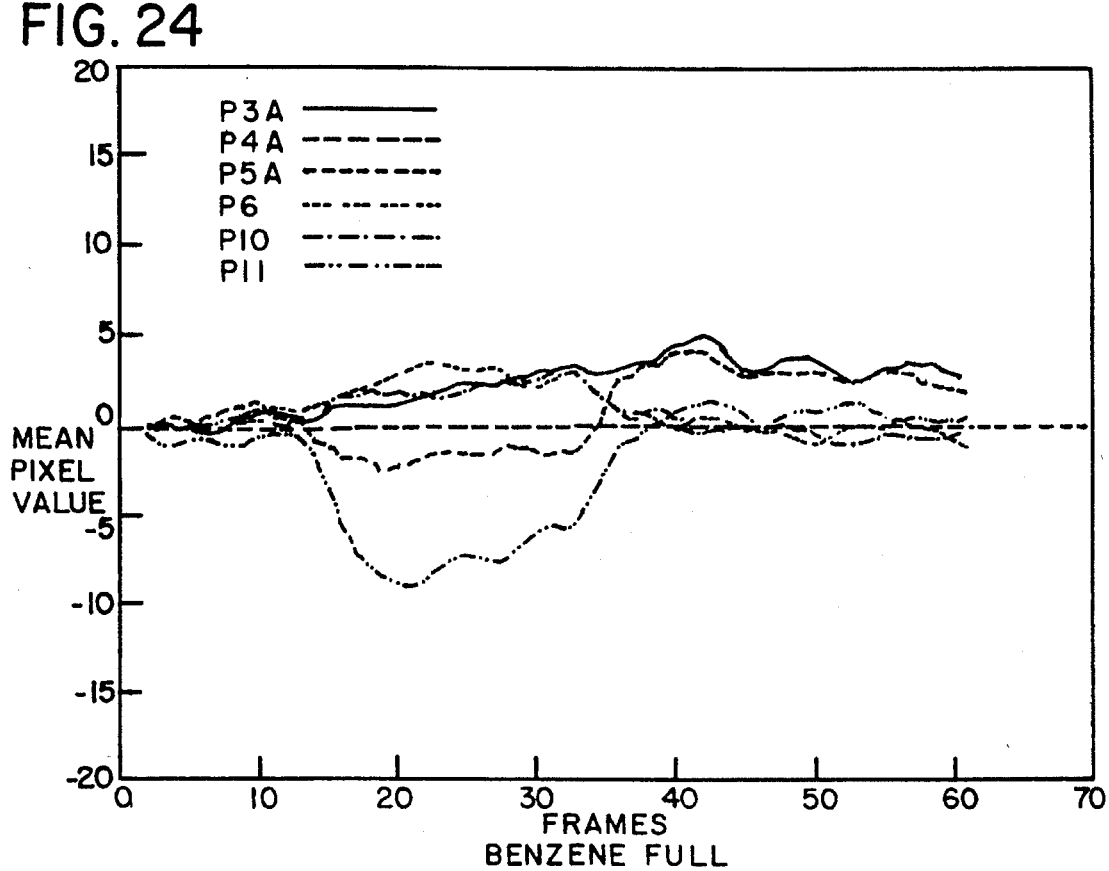
FIG. 24 is a graph illustrating a spectral recognition pattern indicative for benzene using a first grouping of 6 spectral responses from among the 18 spectral responses generated by the optical fiber sensor of FIG. 22.
Figure 25:
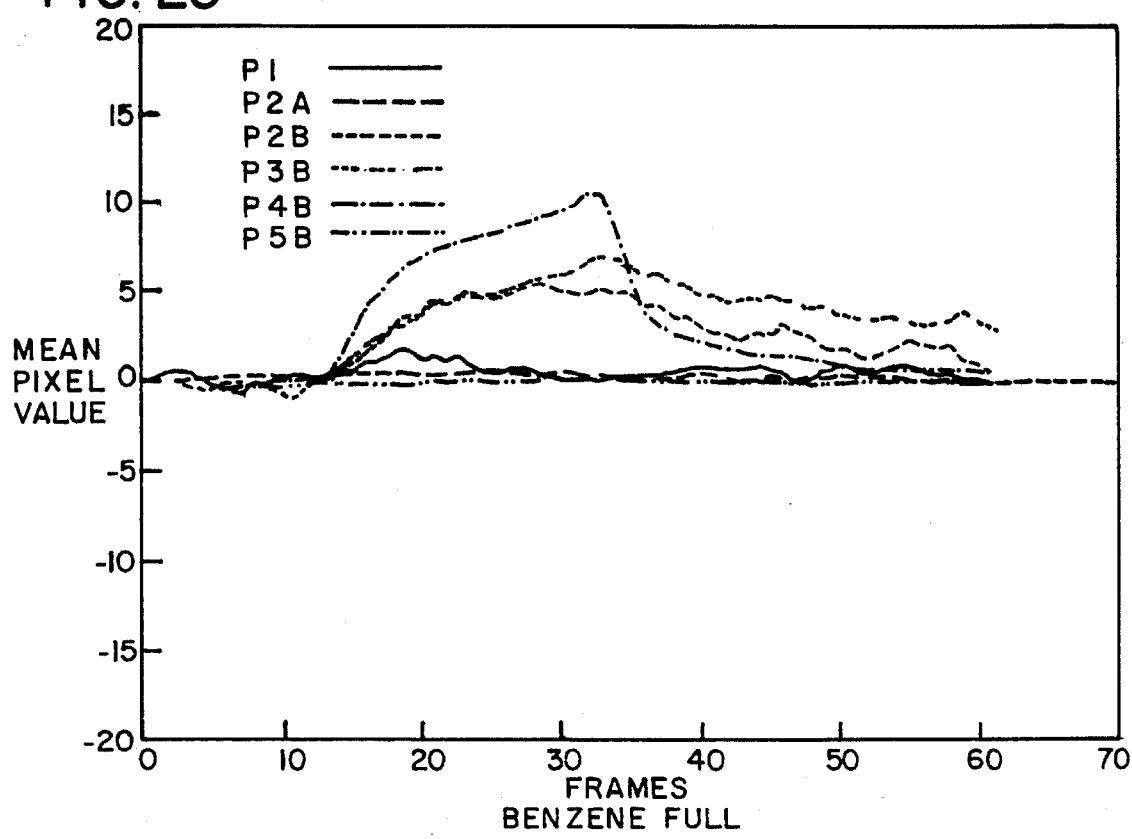
FIG. 25 is a graph illustrating a spectral recognition pattern indicative for benzene using a second grouping of 6 spectral responses from among the 18 spectral responses generated by the optical fiber of FIG. 22.
Figure 26:
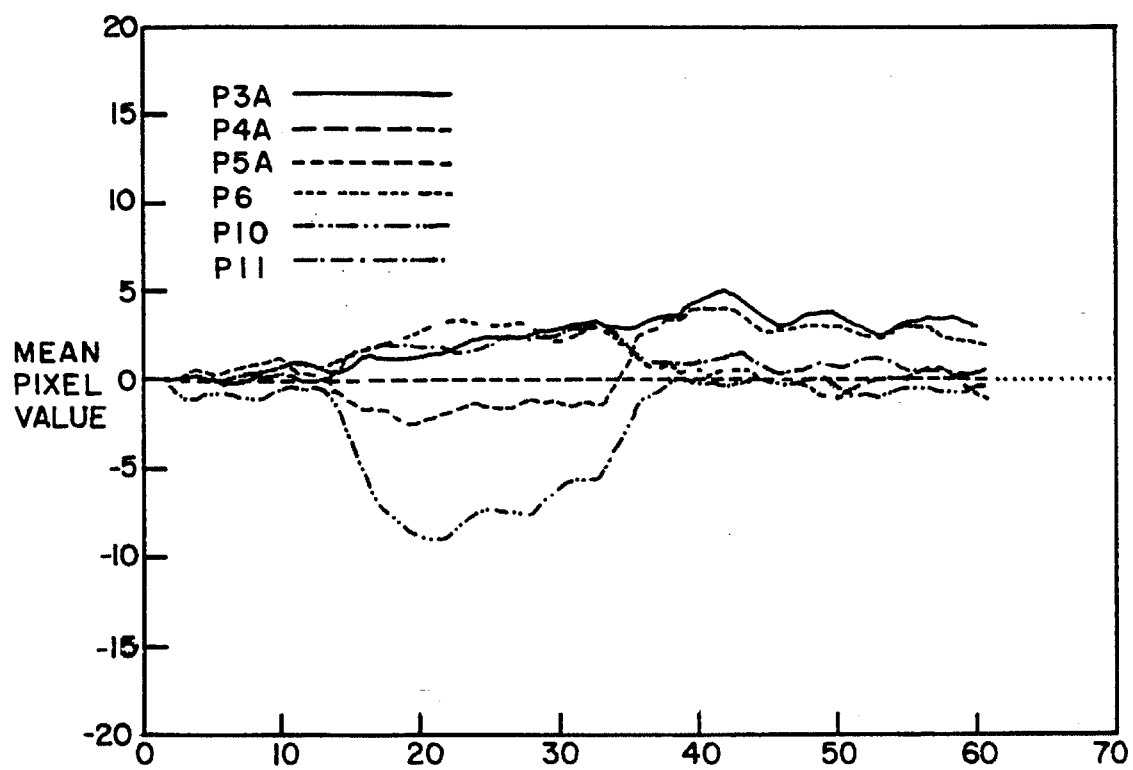
FIG. 26 is a graph illustrating a spectral recognition pattern indicative for benzene using a third grouping of 6 spectral responses from among the 18 spectral responses generated by the optical fiber sensor of FIG. 22.

It will be recognized that FIGS. 24, 25, and 26 illustrate the changes in fluorescent light intensity for different groupings of individual sensing receptor units (polymer/dye combinations) in the optical fiber sensor from the overall total of 18 individual spectral responses actually generated by the array. FIG. 24 reveals the spectral responses in light emission intensity yielded by the array after reaction to benzene for the polymer/dye thin film coatings identified as p3a, p4a, p5a, p6, p10, and p11 respectively as a grouped collection pattern. In comparison, FIG. 25 reveals the grouped collective pattern of spectral responses over time in reaction to benzene provided by the array using only the polymer/dye coatings identified as p1, p2a, p2b, p3b, p4b, and p5b respectively. Lastly, FIG. 26 demonstrates the pattern of spectral responses generated over time by the array in reaction to benzene for only the polymer/dye coatings identified as p7a, p7b, p8a, p8b, p9a, and p9b respectively.

Conclusions

Via the empirical date of FIGS. 24, 25, and 26, it will also be noted and appreciated that the membership of each group forming the collective pattern of spectral responses in each instance has been arbitrarily assigned; and that the user can choose, at will and as he personally wishes, which among the 18 individual spectral responses to use in creating a group or collective spectral recognition pattern by which to identify and distinguish benzene from other similar and dissimilar chemical compounds. In effect, the user may use less than six spectral response to form a spectral recognition pattern from among the 18 spectral responses actually available; or may use any six spectral response progressions among the 18 actually available to form a grouped pattern (as shown by FIGS. 24–26); or may use more than six spectral responses to form a collective recognition pattern; or may (as in distinguishing among homologs of the same chemical compound series) use all 18 spectral responses generated by the optical fiber sensor to form one single spectral recognition pattern.

The present invention is not to be limited in scope nor limited in form except by the claims appended hereto.

What we claim is:

1. An optical sensor for detecting an analyte of interest in a fluid sample, said optical sensor comprising:

a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic array being comprised of a polymeric substance of predetermined chemical composition, and a semi-selective dye compound of predetermined chemical composition which has characteristic spectral properties, is disposed in admixture with said polymeric substance, and can react semi-selectively and spectrally differently over time with more than one analyte, (a) wherein said admixed dye compound absorbs light energy of a predetermined wavelength and, in the presence of said polymeric substance without an analyte able to react semi-selectively, yields a baseline spectral response over time which is optically detectable and recognizable as showing an absence of analyte, and (b) wherein said admixed dye compound absorbs light energy of a predetermined wavelength and, in the presence of said polymeric substance and at least one analyte of interest able to react semi-selectively, generates a modified spectral response over time which is optically detectable and recognizable as showing the spectral consequence of semi-selective reaction with the analyte of interest, said multiple semi-selective sensing receptor units of said optic array presenting a plurality of differing and alternative modified spectral responses after concurrent semi-selective reaction with the analyte of interest in the fluid sample, the spectral pattern formed collectively by said plurality of differing and alternative modified spectral responses resulting in spectral recognition progression pattern means by which to detect and identify that analyte of interest.

2. An optical sensor for detecting a first analyte of interest which is intermixed with at least one other analyte of interest in a fluid sample, said optical sensor comprising:

a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic, array being comprised of a polymeric substance of predetermined chemical composition, and a semi-selective dye compound of predetermined chemical composition which has characteristic spectral properties, is disposed in admixture with said polymeric substance, and can react semi-selectively and spectrally differently over time with more than one analyte, (a) wherein said admixed dye compound absorbs light energy of a predetermined wavelength and, in the presence of said polymeric substance without an analyte able to react semi-selectively, yields a baseline spectral response which is optically detectable and recognizable as showing an absence of analyte, and (b) wherein said admixed dye compound absorbs light energy of a predetermined wavelength and, in the presence of said polymeric substance and a first analyte of interest able to react semi-selectively, generates a first modified spectral response over time which is optically detectable and recognizable as showing the spectral consequence of semi-selective reaction with the first analyte of interest, and (c) wherein said admixed dye compound absorbs light energy of a predetermined wavelength and, in the presence of said polymeric substance and at least a second analyte of interest able to react semi-selectively, generates a second modified spectral response which is optically detectable and recognizable as showing the spectral consequence of semi-selective reaction with the second analyte of interest, said multiple semi-selective sensing receptor units of said optic array presenting a plurality of differing and alternative modified spectral responses after semi-selective reaction with each of said first and second analytes of interest, the spectral pattern formed collectively by said plurality of differing and alternative modified spectral responses for each of said first and second analytes of interest resulting in individual spectral recognition progression pattern means by which to detect and identify each of the analytes of interest in the fluid sample.

3. An optical sensing apparatus for detecting an analyte of interest in a fluid sample, said optical sensing apparatus comprising:

a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic array being comprised of a polymeric substance of predetermined chemical composition, and a semi-selective dye compound of predetermined chemical composition which has characteristic spectral properties, is disposed in admixture with said polymeric substance, and can react semi-selectively and spectrally differently with more than one analyte, (a) wherein said admixed dye compound absorbs light energy of a predetermined wavelength and, in the presence of said polymeric substance without an analyte able to react semi-selectively, yields a baseline spectral response over time which is optically detectable and recognizable as showing an absence of analyte, and (b) wherein said admixed dye compound absorbs light energy of a predetermined wavelength and, in the presence of said polymeric substance and at least one analyte of interest able to react semi-selectively, generates a modified spectral response over time which is optically detectable and recognizable as showing the spectral consequence of semi-selective reaction with the analyte of interest, said multiple semi-selective sensing receptor units of said optic array presenting a plurality of differing and alternative modified spectral responses after concurrent semi-selective reaction with the analyte of interest in the fluid sample, the spectral pattern formed collectively by said plurality of differing and alternative modified spectral responses for an analyte of interest resulting in spectral recognition progression pattern means by which to detect and identify that analyte of interest;

means for introducing a fluid sample to said optic array for semi-selective reactive contact;

means for introducing light energy of a predetermined wavelength to said multiple semi-selective sensing receptor units of said optic array; and computerized optical detection and evaluation means for optically detecting said plurality of differing and alternative modified spectral responses generated by said semi-selective sensing receptor units and for evaluating said resulting spectral recognition progression pattern means to determine the presence of that analyte of interest in the fluid sample.

4. An optical sensing apparatus for detecting a first analyte of interest which is intermixed with at least one other analyte of interest in a fluid sample, said optical sensing apparatus comprising:

a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic array being comprised of a polymeric substance of predetermined chemical composition, and a semi-selective dye compound of predetermined chemical composition which has characteristic spectral properties, is disposed in admixture with said polymeric substance, and can react semi-selectively and spectrally differently over time with more than one analyte, (a) wherein said admixed dye compound absorbs light energy of a predetermined wavelength and, in the presence of said polymeric substance without an analyte able to react semi-selectively, yields a baseline spectral response over time which is optically detectable and recognizable as showing an absence of analyte, and (b) wherein said admixed dye compound absorbs light energy of a predetermined wavelength and, in the presence of said polymeric substance and a first analyte of interest able to react semi-selectively, generates a modified spectral response over time which is optically detectable and recognizable as showing the spectral consequence of semi-selective reaction with the analyte of interest, and (c) wherein said admixed dye compound absorbs light energy of a predetermined wavelength and, in the presence of said polymeric substance and at least a second analyte of interest able to react semi-selectively, generates a second modified spectral response over time which is optically detectable and recognizable as showing the spectral consequence of semi-selective reaction with the second analyte of interest, said multiple semi-selective sensing receptor units of said optic array presenting a plurality of differing and alternative modified spectral responses after concurrent semi-selective reaction with each of the first and second analytes of interest, the spectral pattern formed collectively by said plurality of differing and alternative modified spectral responses for each of the first and second analytes of interest resulting in individual spectral recognition progression pattern means by which to detect and identify each of the analytes of interest in the fluid sample;

means for introducing a fluid sample to said optic array for semi-selective reactive contact;

means for introducing light energy of a predetermined wavelength to said multiple semi-selective sensing receptor units of said optic array; and computerized optical detection and evaluation means for optically detecting said plurality of differing and alternative modified spectral responses generated by said semi-selective sensing receptor units and for evaluating said resulting spectral recognition progression pattern means individually to determine the presence of each of the analytes of interest in the fluid sample.

5. An optical method for detecting an analyte of interest in a fluid sample, said optical method comprising the steps of: providing an optical sensor comprised of a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic array being comprised of (a) a polymeric substance of predetermined chemical composition, and (b) a semi-selective dye compound of predetermined chemical composition which has characteristic spectral properties, is disposed in admixture with said polymeric substance, and can react semi-selectively and spectrally differently over time with more than one analyte, (i) wherein said admixed dye compound absorbs light energy of a predetermined wavelength and, in the presence of said polymeric substance without an analyte able to react semi-selectively, yields a baseline spectral response progression over time which is optically detectable and recognizable as showing an absence of analyte, and (ii) wherein said admixed dye compound absorbs light energy of predetermined wavelength and, in the presence of said polymeric substance and an analyte of interest able to react semi-selectively, generates a modified spectral response over time which is optically detectable and recognizable as showing the spectral consequence of semi-selective reaction with the analyte of interest, said multiple semi-selective sensing receptor units of said optic array presenting a plurality of differing and alternative modified spectral responses after concurrent semi-selective reaction with the analyte of interest, the spectral pattern formed collectively by said plurality of differing and alternative modified spectral responses resulting in spectral recognition progression pattern means by which to detect and identify that analyte of interest;

introducing the fluid sample to said optical sensor for semi-selective reactive contact;

introducing light energy of a predetermined wavelength to said multiple semi-selective sensing receptor units of said optical sensor;

optically detecting said plurality of differing and alternative modified spectral responses generated over time by said semi-selective sensing receptor units of said optical sensor collectively to form said resulting spectral recognition progression pattern means; and evaluating said resulting spectral recognition progression pattern means using computerized means to determine the presence of that analyte of interest in the fluid sample.

6. An optical method for detecting a first analyte of interest which is intermixed with at least one other analyte of interest in a fluid sample, said method comprising the steps of:

providing an optical sensor comprising:

a supporting member; and an optic array formed of multiple semi-selective sensing receptor units which differ in their constituent chemical formulations, which differ in their spectral characteristics, which are immobilized at different spatial positions on said supporting member for reactive contact with the fluid sample, and which react concurrently and semi-selectively but spectrally differently with an individual analyte of interest, each of said multiple semi-selective sensing receptor units of said optic array being comprised of (a) a polymeric substance of predetermined chemical composition, and (b) a semi-selective dye compound of predetermined chemical composition which has characteristic spectral properties, is disposed in admixture with said polymeric substance, and can react semi-selectively and spectrally differently over time with more than one analyte, (i) wherein said admixed dye compound absorbs light energy of a predetermined wavelength and, in the presence of said polymeric substance without an analyte able to react semi-selectively, yields a baseline spectral response over time which is optically detectable and recognizable as showing an absence of analyte, and (ii) wherein said admixed dye compound absorbs light energy of a predetermined wavelength and, in the presence of said polymeric substance and a first analyte of interest able to react semi-selectively, generates a first modified spectral response over time which is optically detectable and recognizable as showing the spectral consequence of semi-selective reaction with the first analyte of interest, and (iii) wherein said admixed dye compound absorbs light energy of a predetermined wavelength and, in the presence of said polymeric substance and at least a second analyte of interest able to react semi-selectively, generates a second modified spectral response over time which is optically detectable and recognizable as showing the spectral consequence of semi-selective reaction with a second analyte of interest, said multiple semi-selective sensing receptor units of said optic array presenting a plurality of differing and alternative modified spectral responses after concurrent semi-selective reaction with each of the first and second analytes of interest, the spectral pattern formed collectively by said plurality of differing and alternative modified spectral responses for each of the first and second analytes of interest resulting in individual spectral recognition progression pattern means by which to detect and identify each of the analytes of interest;

introducing the fluid sample to said optical sensor for semi-selective reactive contact;

introducing light energy of a predetermined wavelength to said multiple semi-selective sensing receptor units of said optical sensor;

optically detecting said plurality of differing and alternative modified spectral responses generated by said semi-selective sensing receptor units of said optical sensor collectively to form individual resulting spectral recognition progression pattern means; and evaluating said resulting spectral recognition progression pattern means individually using computerized means to determine the presence of each of the analytes of interest in the fluid sample.

* * * * *

UNITED STATES PATENT AND TRADEMARK OFFICE
CERTIFICATE OF CORRECTION

PATENT NO.     : 5,512,490
DATED          : April 30, 1996
INVENTOR(S)    : David R. Walt and John S. Kauer Page 1 of 1

It is certified that error appears in the above-identified patent and that said Letters Patent is hereby corrected as shown below:

Column 1,
Line 6, after the title "OPTICAL SENSOR, OPTICAL SENSING APPARATUS, AND METHODS FOR DETECTING AN ANALYTE OF INTEREST USING SPECTRAL RECOGNITION PATTERNS, insert the following paragraph:

-- This invention was made with government support under N00014-95-1-1340 awarded by the Department of the Navy, Office of Naval Research. The government has certain rights in the invention. --

Signed and Sealed this

Twenty-first Day of May, 2002

*Attest:*

*Attesting Officer*

JAMES E. ROGAN
*Director of the United States Patent and Trademark Office*